(12) United States Patent
Kang et al.

(10) Patent No.: US 11,845,973 B2
(45) Date of Patent: Dec. 19, 2023

(54) POLY(3-HYDROXYPROPIONATE-B-LACTATE) BLOCK COPOLYMER USING MICROORGANISMS

(71) Applicant: LG CHEM, LTD., Seoul (KR)

(72) Inventors: Hye Ok Kang, Daejeon (KR); Donggyun Kang, Daejeon (KR); Chul Woong Kim, Daejeon (KR); In Young Huh, Daejeon (KR); Jung Yun Choi, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 17/679,007

(22) Filed: Feb. 23, 2022

(65) Prior Publication Data

US 2022/0251612 A1 Aug. 11, 2022

Related U.S. Application Data

(62) Division of application No. 16/754,480, filed as application No. PCT/KR2019/002909 on Mar. 13, 2019, now Pat. No. 11,286,510.

(30) Foreign Application Priority Data

Mar. 15, 2018 (KR) .................. 10-2018-0030522

(51) Int. Cl.
| | | |
|---|---|---|
| *C08G 63/06* | (2006.01) | |
| *C12P 7/625* | (2022.01) | |
| *C12N 1/20* | (2006.01) | |
| *C12N 15/70* | (2006.01) | |
| *C12N 9/04* | (2006.01) | |
| *C12N 9/02* | (2006.01) | |
| *C12N 9/10* | (2006.01) | |
| *C08G 63/08* | (2006.01) | |
| *C12N 9/88* | (2006.01) | |

(52) U.S. Cl.
CPC .............. *C12P 7/625* (2013.01); *C08G 63/06* (2013.01); *C08G 63/08* (2013.01); *C12N 1/20* (2013.01); *C12N 9/0006* (2013.01); *C12N 9/0008* (2013.01); *C12N 9/1029* (2013.01); *C12N 9/13* (2013.01); *C12N 9/88* (2013.01); *C12N 15/70* (2013.01); *C12Y 101/01027* (2013.01); *C12Y 101/01028* (2013.01); *C12Y 102/01003* (2013.01); *C12Y 203/01* (2013.01); *C12Y 208/03001* (2013.01); *C12Y 402/0103* (2013.01); *C12Y 402/01036* (2013.01); *C12N 2510/02* (2013.01)

(58) Field of Classification Search
USPC ................................................. 528/271, 272
See application file for complete search history.

(56) References Cited

U.S. PATENT DOCUMENTS

| | | | |
|---|---|---|---|
| 8,685,701 | B2 | 4/2014 | Yang et al. |
| 8,802,814 | B2 | 8/2014 | Le et al. |
| 8,809,027 | B1 | 8/2014 | Lynch et al. |
| 2002/0164729 | A1 | 11/2002 | Skraly et al. |
| 2007/0277268 | A1 | 11/2007 | Cho et al. |
| 2009/0176938 | A1 | 7/2009 | Xu et al. |
| 2009/0226988 | A1 | 9/2009 | Tajima et al. |
| 2010/0021919 | A1 | 1/2010 | Skraly et al. |
| 2010/0136637 | A1 | 6/2010 | Park et al. |
| 2011/0046339 | A1* | 2/2011 | Park ................. C08G 63/06 435/135 |
| 2011/0177569 | A1 | 7/2011 | Park et al. |
| 2012/0329110 | A1 | 12/2012 | Kim et al. |
| 2014/0030774 | A1 | 1/2014 | Park et al. |

(Continued)

FOREIGN PATENT DOCUMENTS

| | | |
|---|---|---|
| JP | 2009138174 A | 6/2009 |
| JP | 2010-510372 A | 4/2010 |
| JP | 2010-536338 A | 12/2010 |

(Continued)

OTHER PUBLICATIONS

Kenney, J.F., "Properties of Block Versus Random Copolymers," Polymer Engineering and Science, 8(3):216-226 (1968).

(Continued)

*Primary Examiner* — Terressa Boykin

(74) *Attorney, Agent, or Firm* — Bryan Cave Leighton Paisner LLP

(57) ABSTRACT

The present invention relates to a novel 3-hydroxypropionate-lactate block copolymer [P(3HP-b-LA)], and a method for preparing same, and more specifically, provides a method for preparing a 3-hydroxypropionate-lactate block copolymer, and a 3-hydroxypropionate-lactate block copolymer produced thereby, the method comprising: a first culture step in which, by using recombinant E. coli improved so as to be incapable of biosynthesizing lactic acid, P(3HP) is biosynthesized at the early stage of culturing by having glycerol as a carbon source and through 3-hydroxypropionate-generating genes and an enhanced PHA synthase; and a second culture step in which P(3HP) production is inhibited by using a carbon catabolic repression system for selectively introducing only glucose into E. coli when glycerol and glucose are supplied together as carbon sources, and in which polylactate is biosynthesized to an interrupted P(3HP) terminus by the enabling of the expression of a lactate synthase and a lactyl-CoA converting enzyme through an IPTG induction system.

1 Claim, 6 Drawing Sheets

Specification includes a Sequence Listing.

(56) References Cited

U.S. PATENT DOCUMENTS

| | | |
|---|---|---|
| 2015/0031098 A1 | 1/2015 | Park et al. |
| 2016/0312251 A1 | 10/2016 | Park et al. |

FOREIGN PATENT DOCUMENTS

| | | |
|---|---|---|
| JP | 2011032547 A | 2/2011 |
| JP | 2012-516695 A | 7/2012 |
| KR | 10-20040014389 | 2/2004 |
| KR | 10-20060121555 | 11/2006 |
| KR | 10-20080046795 | 5/2008 |
| KR | 10-20090078925 | 7/2009 |
| KR | 10-2009-0127516 A | 12/2009 |
| KR | 100957773 | 5/2010 |
| KR | 10-20100112610 | 10/2010 |
| KR | 10-20130071395 | 6/2013 |
| KR | 10-20140018244 | 2/2014 |
| KR | 10-20170028189 | 3/2017 |
| KR | 10-20190084576 | 7/2019 |
| WO | 2009022797 | 2/2009 |

OTHER PUBLICATIONS

Park et al., "Metabolic engineering of Ralstonia eutropha for the biosynthesis of 2-hydroxyacid-containing polyhydroxyalkanoates," Metabolic Engineering 20:20-28 (2013).

Sambrook et al., "Molecular cloning: a laboratory manual," 2nd Edition, Cold Spring Harbor Laboratory Press, Cold Spring Harbor, New York (1989), Abstract, 2 pages.

Lee et al., "Comparison of Recombinant *Escherichia coli* Strains for Synthesis and Accumulation of Poly-(3-Hydroxybutyric Acid) and Morphological Changes," Biotechnology and Bioengineering, 44:1337-1347 (1994).

Zhou, et al."Functional Replacement of the *Escherichia coli* d-(−)-Lactate Dehydrogenase Gene (IdhA) with the I-(+)-Lactate Dehydrogenase Gene (IdhL) from Pediococcus acidilactici†", Appl Environ Microbiol. 69, 2003, 2237-2244, 2003.

Schweiger, "On the dehydration of (R)-lactate in the fermentation of Alanine to Propionate by Clostridium Propionicum", FEBS 171, 1984, 79-84, 1984.

Casarano, et al."Block Copolymers Containing (R)-3-Hydroxybutyrate and Isosorbide Succinate or (S)-Lactic Acid Mers". Journal of Polymers and the Environment; vol. 18, 2010, 33-44, 2010.

Andreeben, et al. "Biosynthesis and Biodegradation of 3-Hydroxypropionate-Containing Polyesters" Appl Environ Microbiol, 76, 4919-25, 2010.

Ochi, et al. Engineering of Class I Lactate-Polymerizing Polyhydroxyalkanoate Synthases From Ralstonia Eutropha That Synthesize Lactate-Based Polyester With a Block Nature, Applied Microbiology and Biotechnology, vol. 97, 3441-3447, 2013.

Wang, et al. "Production of Block Copolymer Poly(3-hydroxybutyrate)-block-poly(3-hydroxypropionate) with Adjustable Structure from an Inexpensive Carbon Source"; ACS Macro Letters. 2., 996-1000, 2013.

Donovan. et al. Review: Optimizing Inducer and Culture Conditions for Expression of Foreign Proteins Under the Control of The Lac Promoter, J Ind Microbiol, vol. 16, 145-54, 1996.

\* cited by examiner

[FIG. 1]
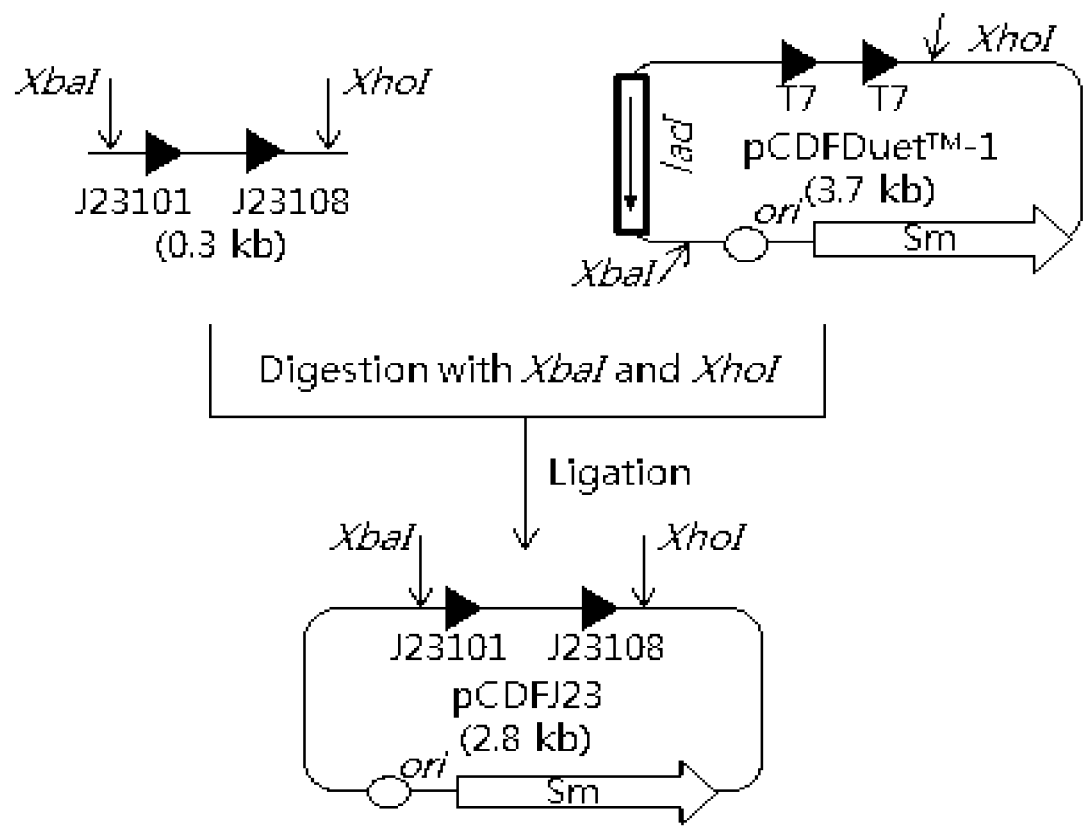

[FIG. 2]
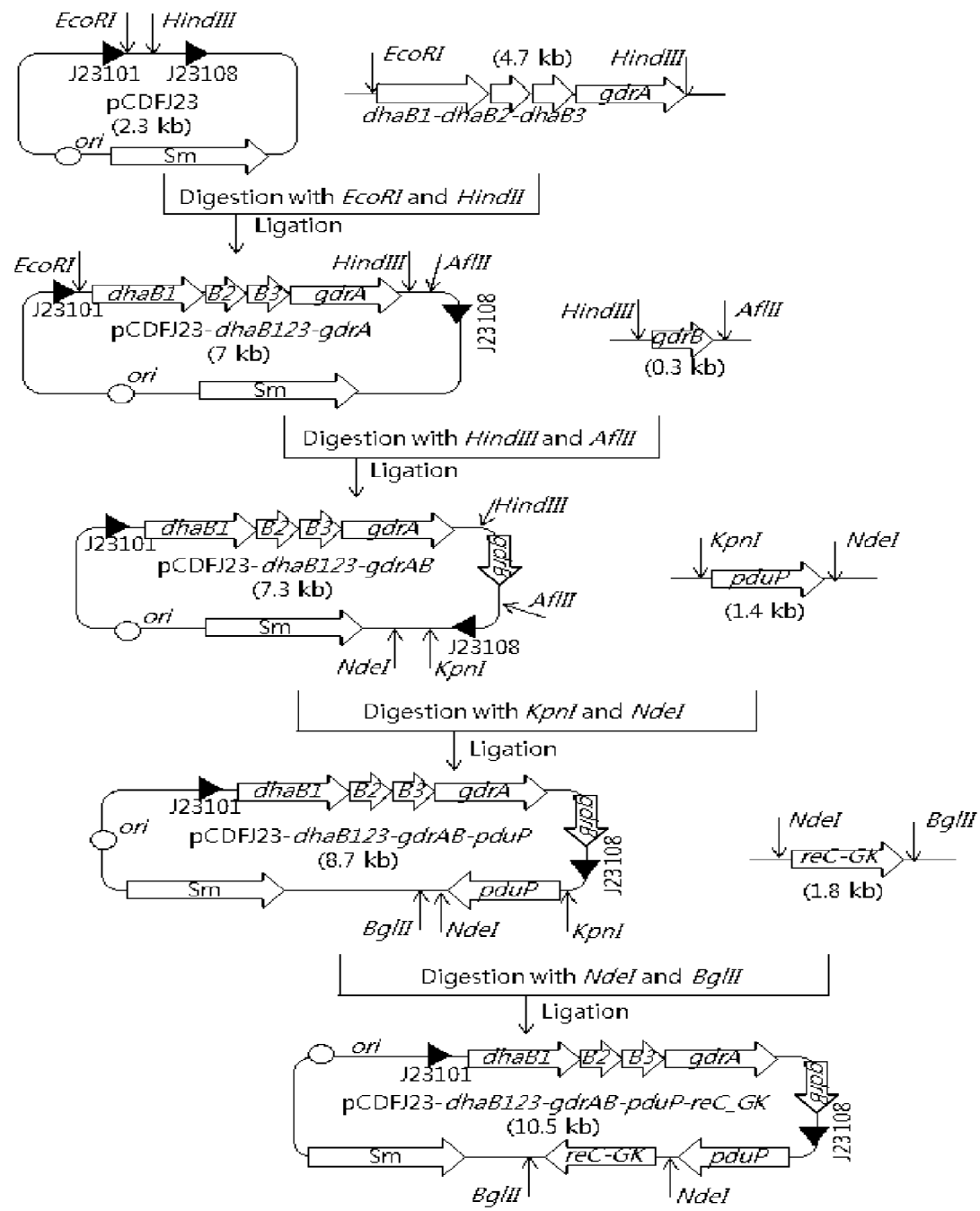

[FIG. 3]
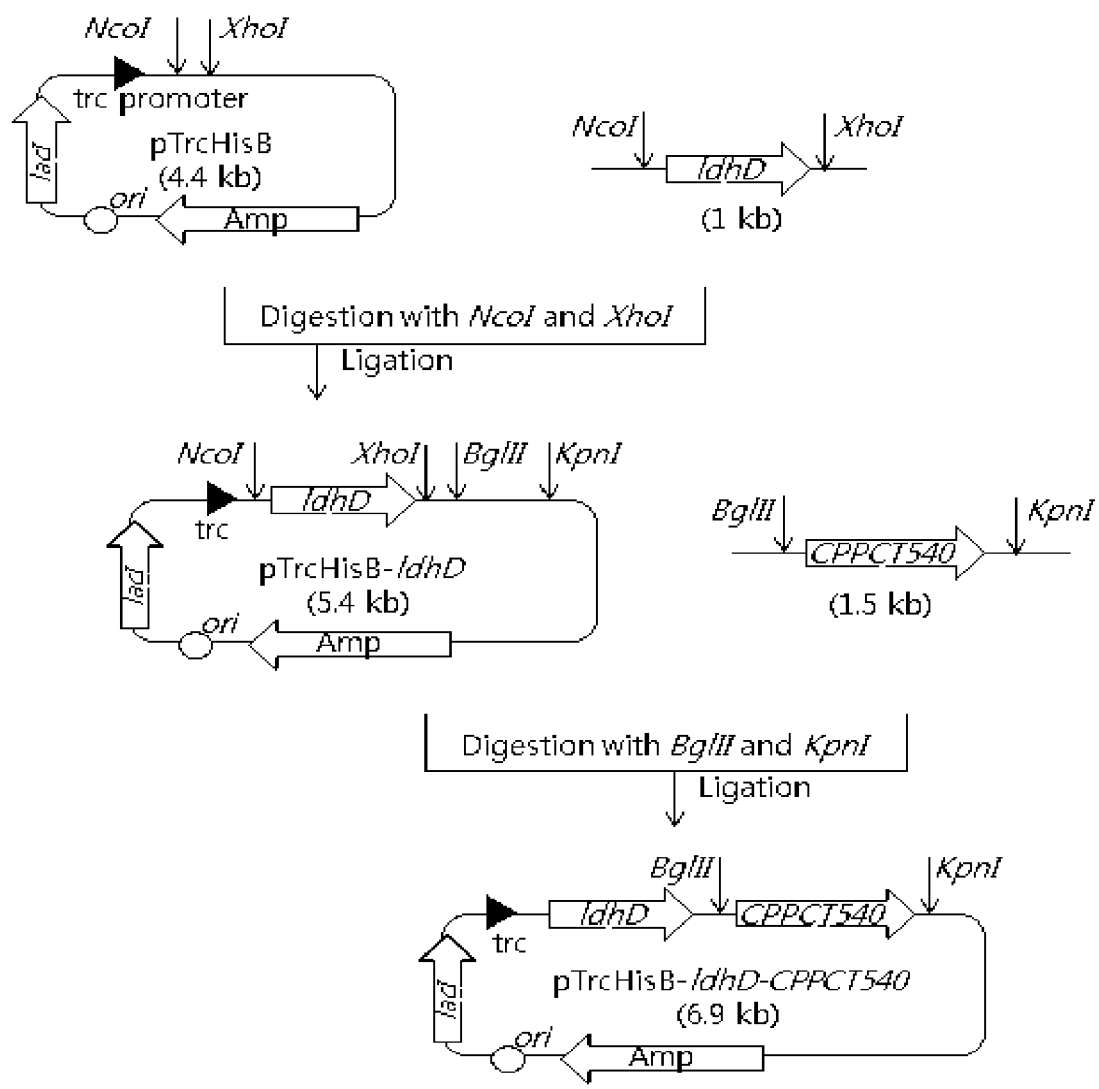

[FIG. 4]
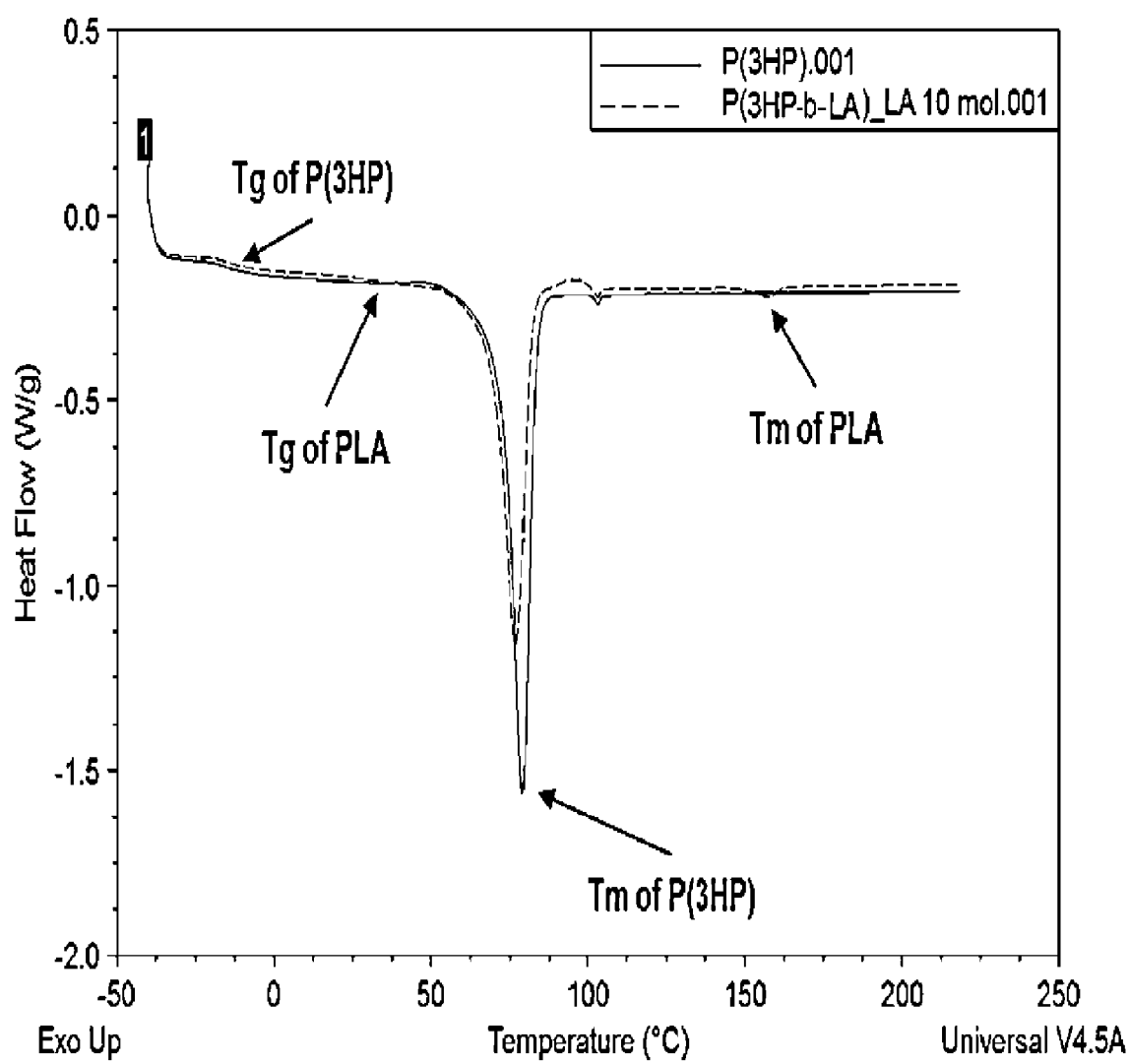

[FIG. 5]
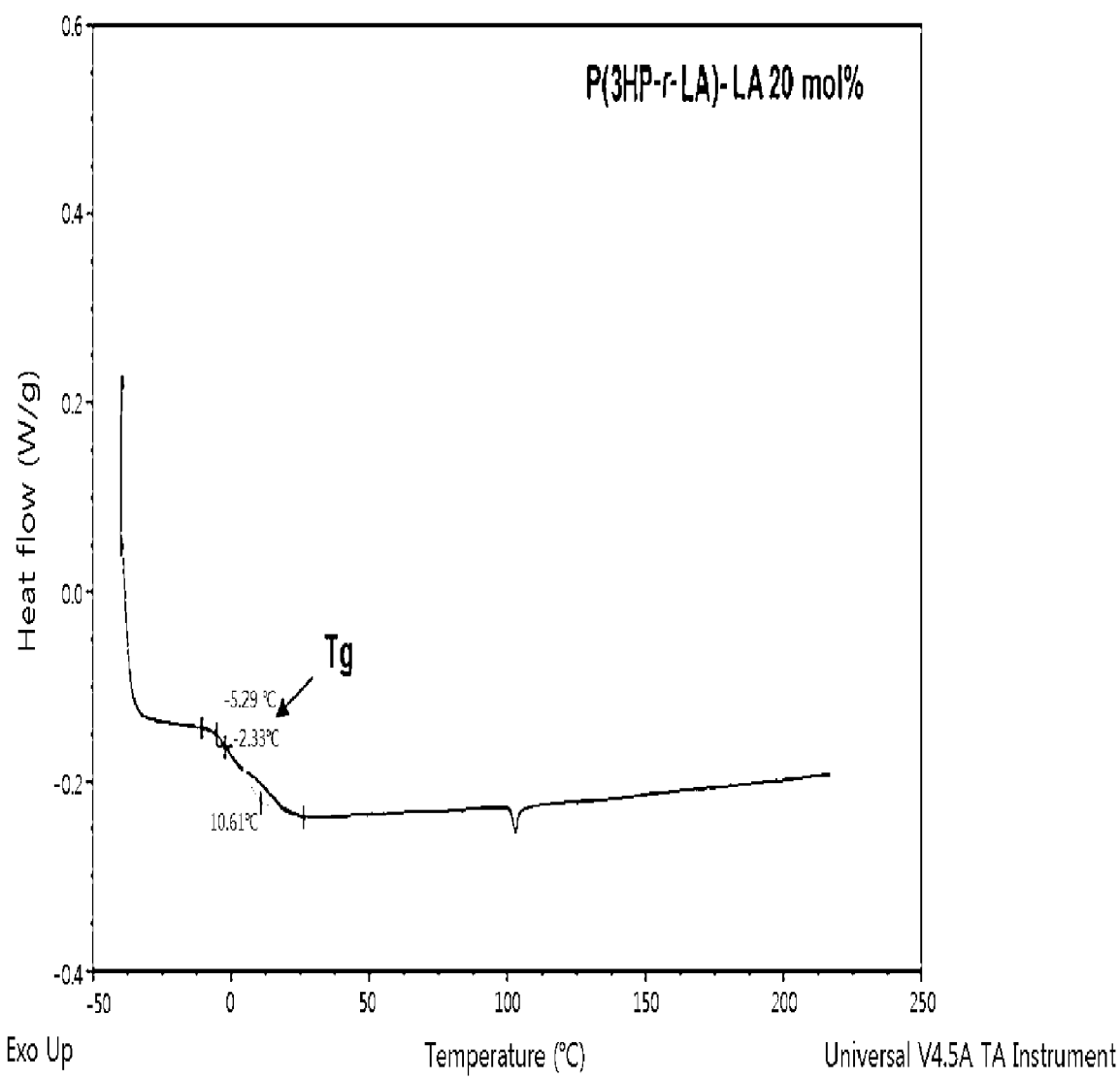

[FIG. 6]
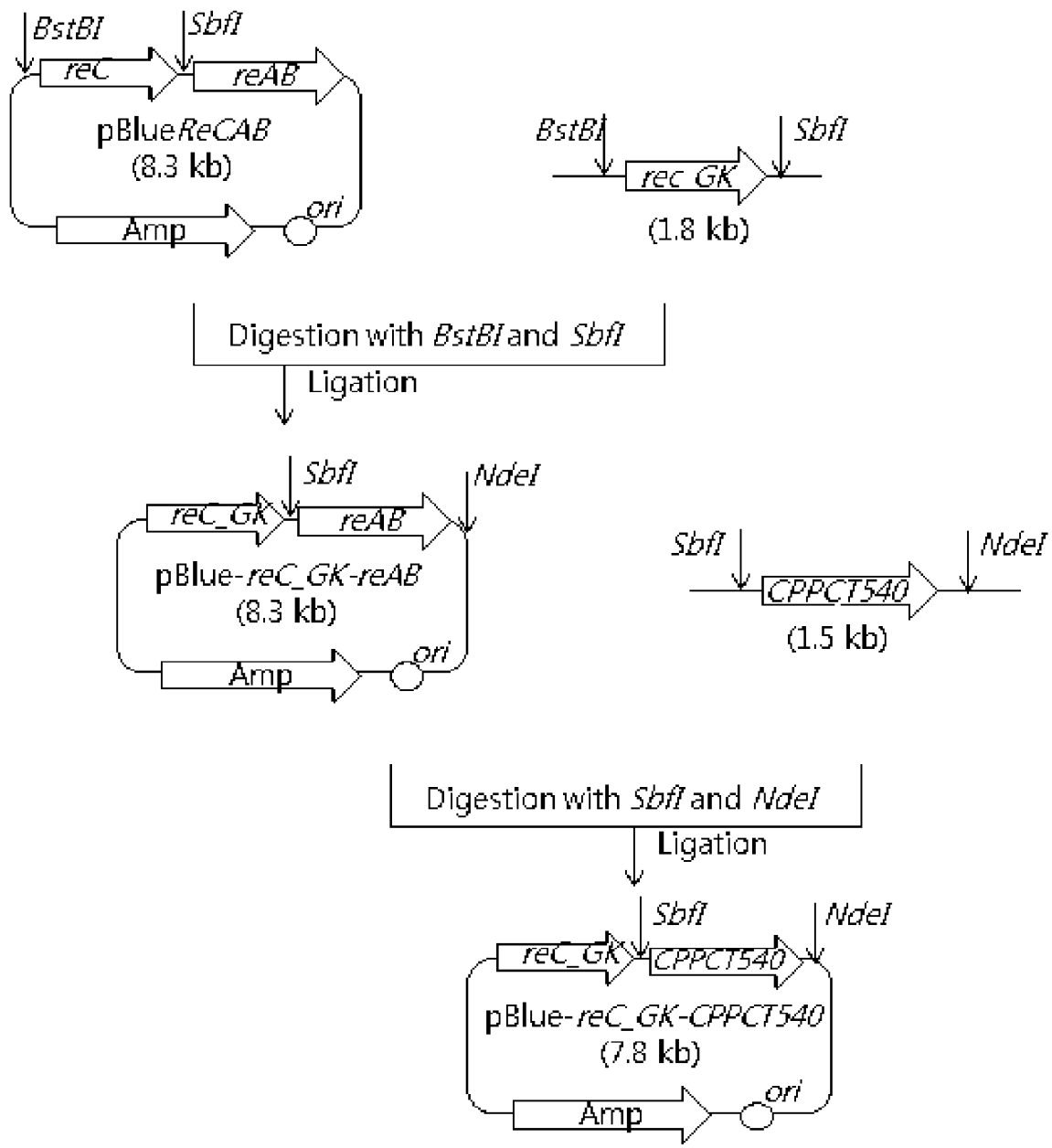

SEQUENCE LISTING

<160> NUMBER OF SEQ ID NOS: 41

<210> SEQ ID NO 1
<211> LENGTH: 552
<212> TYPE: PRT
<213> ORGANISM: Artificial Sequence
<220> FEATURE:
<223> OTHER INFORMATION: DhaB1

<400> SEQUENCE: 1

```
Met Lys Arg Ser Lys Arg Phe Ala Val Leu Ala Gln Arg Pro Val Asn
1               5                   10                  15

Gln Asp Gly Leu Ile Gly Glu Trp Pro Glu Glu Gly Leu Ile Ala Met
            20                  25                  30

Asp Ser Pro Phe Asp Pro Val Ser Ser Val Lys Val Asp Asn Gly Leu
        35                  40                  45
```

```
Ile Val Glu Leu Asp Gly Lys Arg Arg Asp Gln Phe Asp Met Ile Asp
 50                  55                  60

Arg Phe Ile Ala Asp Tyr Ala Ile Asn Val Glu Arg Thr Glu Gln Ala
 65                  70                  75                  80

Met Arg Leu Glu Ala Val Glu Ile Ala Arg Met Leu Val Asp Ile His
                 85                  90                  95

Val Ser Arg Glu Glu Ile Ile Ala Ile Thr Thr Ala Ile Thr Pro Ala
                100                 105                 110

Lys Ala Val Glu Val Met Ala Gln Met Asn Val Val Glu Met Met Met
                115                 120                 125

Ala Leu Gln Lys Met Arg Ala Arg Arg Thr Pro Ser Asn Gln Cys His
130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Glu Thr Thr Val Gly Ile
                165                 170                 175

Ala Arg Tyr Ala Pro Phe Asn Ala Leu Ala Leu Leu Val Gly Ser Gln
                180                 185                 190

Cys Gly Arg Pro Gly Val Leu Thr Gln Cys Ser Val Glu Glu Ala Thr
                195                 200                 205

Glu Leu Glu Leu Gly Met Arg Gly Leu Thr Ser Tyr Ala Glu Thr Val
                210                 215                 220

Ser Val Tyr Gly Thr Glu Ala Val Phe Thr Asp Gly Asp Asp Thr Pro
225                 230                 235                 240

Trp Ser Lys Ala Phe Leu Ala Ser Ala Tyr Ala Ser Arg Gly Leu Lys
                245                 250                 255

Met Arg Tyr Thr Ser Gly Thr Ala Leu Met Gly Tyr Ser Glu Ser Lys
                260                 265                 270

Ser Met Leu Tyr Leu Glu Ser Arg Cys Ile Phe Ile Thr Lys Gly Ala
                275                 280                 285

Gly Val Gln Gly Leu Gln Asn Gly Ala Val Ser Cys Ile Gly Met Thr
                290                 295                 300

Gly Ala Val Pro Ser Gly Ile Arg Ala Val Leu Ala Glu Asn Leu Ile
305                 310                 315                 320

Ala Ser Met Leu Asp Leu Glu Val Ala Ser Ala Asn Asp Gln Thr Phe
                325                 330                 335

Ser His Ser Asp Ile Arg Arg Thr Ala Arg Thr Leu Met Gln Met Leu
                340                 345                 350

Pro Gly Thr Asp Phe Ile Phe Ser Gly Tyr Ser Ala Val Pro Asn Tyr
                355                 360                 365

Asp Asn Met Phe Ala Gly Ser Asn Phe Asp Ala Glu Asp Phe Asp Asp
370                 375                 380

Tyr Asn Ile Leu Gln Arg Asp Leu Met Val Asp Gly Gly Leu Arg Pro
385                 390                 395                 400

Val Thr Glu Ala Glu Thr Ile Ala Ile Arg Gln Lys Ala Ala Arg Ala
                405                 410                 415

Ile Gln Ala Val Phe Arg Glu Leu Gly Leu Pro Pro Ile Ala Asp Glu
                420                 425                 430

Glu Val Glu Ala Ala Thr Tyr Ala His Gly Ser Asn Glu Met Pro Pro
                435                 440                 445

Arg Asn Val Val Glu Asp Leu Ser Ala Val Glu Glu Met Met Lys Arg
450                 455                 460

Asn Ile Thr Gly Leu Asp Ile Val Gly Ala Leu Ser Arg Ser Gly Phe
```

```
                465                 470                 475                 480
Glu Asp Ile Ala Ser Asn Ile Leu Asn Met Leu Arg Gln Arg Val Thr
                    485                 490                 495
Gly Asp Tyr Leu Gln Thr Ser Ala Ile Leu Asp Arg Gln Phe Glu Val
            500                 505                 510
Val Ser Ala Val Asn Asp Ile Asn Asp Tyr Gln Gly Pro Gly Thr Gly
        515                 520                 525
Tyr Arg Ile Ser Ala Glu Arg Trp Ala Glu Ile Lys Asn Ile Pro Gly
    530                 535                 540
Val Val Gln Pro Asp Thr Ile Glu
545                 550

<210> SEQ ID NO 2
<211> LENGTH: 1659
<212> TYPE: DNA
<213> ORGANISM: Artificial Sequence
<220> FEATURE:
<223> OTHER INFORMATION: dhaB1 gene

<400> SEQUENCE: 2
atgaaaagat caaaacgatt tgcagtactg gcccagcgcc ccgtcaatca ggacgggctg      60
attggcgagt ggcctgaaga ggggctgatc gccatggaca gcccctttga cccggtctct     120
tcagtaaaag tggacaacgg tctgatcgtc gaactggacg gcaaacgccg ggaccagttt     180
gacatgatcg accggtttat cgccgattac gcgatcaacg ttgaacgcac agagcaggca     240
atgcgcctgg aggcggtgga aatagcccgc atgctggtgg atattcacgt cagccgggag     300
gagatcattg ccatcactac cgccatcacg ccggccaaag cggtcgaggt gatggcgcag     360
atgaacgtgg tggagatgat gatggcgctg cagaagatgc gtgcccgccg acccccctcc     420
aaccagtgcc acgtcaccaa tctcaaagat aatccggtgc agattgccgc tgacgccgcc     480
gaggccggga tccgcggctt ctcagaacag gagaccacgg tcggtatcgc gcgctacgcg     540
ccgtttaacg ccctggcgct gttggtcggt tcgcagtgcg gccgcccgg cgtgttgacg     600 cagtgctcgg tggaagaggc caccgagctg gagctgggca tgcgtggctt aaccagctac     660
gccgagacgg tgtcggtata cggcacggaa gcggtattta ccgacggcga tgatacgccg     720
tggtcaaagg cgttcctcgc ctcggcctac gcctcccgcg ggttgaaaat cgctacacc     780 tccggcacag cgctgatggg ctattcggag agcaagtcga tgctctacct cgaatcgcgc     840
tgcatcttca ttactaaagg cgccggggtt cagggactgc aaaacggcgc ggtgagctgt     900
atcggcatga ccggcgctgt gccgtcgggc attcggcgg tgctggcgga aaacctgatc     960
gcctctatgc tcgacctcga agtggcgtcc gccaacgacc agactttctc ccactcggat    1020
attgccgcca ccgcgcgcac cctgatgcag atgctgccgg caccgacttt atttctctcc    1080
ggctacagcg cggtgccgaa ctacgacaac atgttcgccg gctcgaactt cgatgcggaa    1140
gattttgatg attacaacat cctgcagcgt gacctgatgt tgacggcgg cctgcgtccg    1200 gtgaccgagg cggaaaccat tgccattcgc cagaaagcgg cgcgggcgat ccaggcggtt    1260
ttccgcgagc tggggctgcc gccaatcgcc gacgaggagg tggaggccgc cacctacgcg    1320
cacggcagca acgagatgcc gccgcgtaac gtggtggagg atctgagtgc ggtggaagag    1380
atgatgaagc gcaacatcac cggcctcgat attgtcggcg cgctgagccg cagcggcttt    1440
gaggatatcg ccagcaatat tctcaatatg ctgcgccagc gggtcaccgg cgattacctg    1500
cagacctcgg ccattctcga tcggcagttc gaggtggtga gtgcggtcaa cgacatcaat    1560
```

```
gactatcagg ggccgggcac cggctatcgc atctctgccg aacgctgggc ggagatcaaa    1620
aatattccgg gcgtggttca gcctgacacc attgaataa                          1659
```

<210> SEQ ID NO 3
<211> LENGTH: 194
<212> TYPE: PRT
<213> ORGANISM: Artificial Sequence
<220> FEATURE:
<223> OTHER INFORMATION: DhaB2

<400> SEQUENCE: 3

```
Met Gln Gln Thr Thr Gln Ile Gln Pro Ser Phe Thr Leu Lys Thr Arg
1               5                   10                  15

Glu Gly Gly Val Ala Ser Ala Asp Glu Arg Ala Asp Glu Val Val Ile
            20                  25                  30

Gly Val Gly Pro Ala Phe Asp Lys His Gln His His Thr Leu Ile Asp
        35                  40                  45

Met Pro His Gly Ala Ile Leu Lys Glu Leu Ile Ala Gly Val Glu Glu
    50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
    130                 135                 140

Lys Glu Ser Pro Ser Pro Val Pro Val Asn Asp Gln Met Val Arg
145                 150                 155                 160

Pro Lys Phe Met Ala Lys Ala Ala Leu Phe His Ile Lys Glu Thr Lys
                165                 170                 175

His Val Val Gln Asp Ala Glu Pro Val Thr Leu His Val Asp Leu Val
            180                 185                 190

Arg Glu
```

<210> SEQ ID NO 4
<211> LENGTH: 585
<212> TYPE: DNA
<213> ORGANISM: Artificial Sequence
<220> FEATURE:
<223> OTHER INFORMATION: dhaB2 gene

<400> SEQUENCE: 4

```
gtgcaacaga caacccaaat tcagccctct tttaccctga aaacccgcga gggcggggta      60
gcttctgccg atgaacgtgc cgatgaagtg gtgatcggcg tcggccctgc cttcgataaa    120
caccagcatc acactctgat cgatatgccc catggcgcga tcctcaaaga gctgattgcc    180
ggggtggaag aagaggggct tcacgcccgg gtggtgcgca ttctgcgcac gtccgacgtc    240
tcctttatgg cctgggatgc ggccaacctg agcggctcgg gatcggcat cggtatccag    300 tcgaagggga ccacggtcat ccatcagcgc gatctgctgc cgctcagcaa cctggagctg    360
ttctcccagg cgccgctgct gacgctggag acctaccggc agattggcaa aaacgccgcg    420
cgctatgcgc gcaaagagtc accttcgccg gtgccggtgg tgaacgacca gatggtgcgg    480
ccgaaattta tggccaaagc cgcactattt catatcaaag agaccaaaca tgtggtgcag    540
```

```
gacgccgagc cgtcaccct gcacgtcgac ttagtaaggg agtga                  585
```

```
<210> SEQ ID NO 5
<211> LENGTH: 143
<212> TYPE: PRT
<213> ORGANISM: Artificial Sequence
<220> FEATURE:
<223> OTHER INFORMATION: DhaB3

<400> SEQUENCE: 5
```

```
Met Thr Met Ser Glu Lys Thr Met Arg Val Gln Asp Tyr Pro Leu Ala
1               5                   10                  15

Thr Arg Cys Pro Glu His Ile Leu Thr Pro Thr Gly Lys Pro Leu Thr
            20                  25                  30

Asp Ile Thr Leu Glu Lys Val Leu Ser Gly Glu Val Gly Pro Gln Asp
        35                  40                  45

Val Arg Ile Ser Arg Gln Thr Leu Glu Tyr Gln Ala Gln Ile Ala Glu
    50                  55                  60

Gln Met Gln Arg His Ala Val Ala Arg Asn Phe Arg Arg Ala Ala Glu
65                  70                  75                  80

Leu Ile Ala Ile Pro Asp Glu Arg Ile Leu Ala Ile Tyr Asn Ala Leu
                85                  90                  95

Arg Pro Phe Arg Ser Ser Gln Ala Glu Leu Leu Ala Ile Ala Asp Glu
            100                 105                 110

Leu Glu His Thr Trp His Ala Thr Val Asn Ala Ala Phe Val Arg Glu
        115                 120                 125

Ser Ala Glu Val Tyr Gln Gln Arg His Lys Leu Arg Lys Gly Ser
    130                 135                 140
```

```
<210> SEQ ID NO 6
<211> LENGTH: 432
<212> TYPE: DNA
<213> ORGANISM: Artificial Sequence
<220> FEATURE:
<223> OTHER INFORMATION: dhaB3 gene

<400> SEQUENCE: 6
```

```
gtgaccatga gcgagaaaac catgcgcgtg caggattatc cgttagccac ccgctgcccg    60
gagcatatcc tgacgcctac cggcaaacca ttgaccgata ttaccctcga gaaggtgctc   120
tctggcgagg tgggcccgca ggatgtgcgg atctcccgtc agacccttga gtaccaggcg   180
cagattgccg agcagatgca gcgccatgcg gtggcgcgca atttccgccg cgcggcggag   240
cttatcgcca ttcctgacga gcgcattctg ctatctata cgcgctgcg cccgttccgc    300 tcctcgcagg cggagctgct ggcgatcgcc gacgagctgg agcacacctg gcatgcgaca   360
gtgaatgccg cctttgtccg ggagtcggcg gaagtgtatc agcagcggca taagctgcgt   420
aaaggaagct aa                                                      432
```

```
<210> SEQ ID NO 7
<211> LENGTH: 607
<212> TYPE: PRT
<213> ORGANISM: Artificial Sequence
<220> FEATURE:
<223> OTHER INFORMATION: GdrA

<400> SEQUENCE: 7
```

```
Met Pro Leu Ile Ala Gly Ile Asp Ile Gly Asn Ala Thr Thr Glu Val
1               5                   10                  15
```

```
Ala Leu Ala Ser Asp Asp Pro Gln Ala Arg Ala Phe Val Ala Ser Gly
                20                  25                  30

Ile Val Ala Thr Thr Gly Met Lys Gly Thr Arg Asp Asn Ile Ala Gly
             35                  40                  45

Thr Leu Ala Ala Leu Glu Gln Ala Leu Ala Lys Thr Pro Trp Ser Met
 50                  55                  60

Ser Asp Val Ser Arg Ile Tyr Leu Asn Glu Ala Val Pro Val Ile Gly
 65                  70                  75                  80

Asp Val Ala Met Glu Thr Ile Thr Glu Thr Ile Ile Thr Glu Ser Thr
                 85                  90                  95

Met Ile Gly His Asn Pro Gln Thr Pro Gly Gly Val Gly Val Gly Val
                100                 105                 110

Gly Thr Thr Ile Ala Leu Gly Arg Leu Ala Thr Leu Pro Ala Ala Gln
            115                 120                 125

Tyr Ala Glu Gly Trp Ile Val Leu Ile Asp Asp Ala Val Asp Phe Leu
            130                 135                 140

Asp Ala Val Trp Trp Leu Asn Glu Ala Leu Asp Arg Gly Ile Asn Val
145                 150                 155                 160

Val Ala Ala Ile Leu Lys Lys Asp Asp Gly Val Leu Val Asn Asn Arg
                165                 170                 175

Leu Arg Lys Thr Leu Pro Val Val Asp Glu Val Thr Leu Leu Glu Gln
                180                 185                 190

Val Pro Glu Gly Val Met Ala Ala Val Glu Val Ala Ala Pro Gly Gln
            195                 200                 205

Val Val Arg Ile Leu Ser Asn Pro Tyr Gly Ile Ala Thr Phe Phe Gly
            210                 215                 220

Leu Ser Pro Glu Glu Thr Gln Ala Ile Val Pro Ile Ala Arg Ala Leu
225                 230                 235                 240

Ile Gly Asn Arg Ser Ala Val Val Leu Lys Thr Pro Gln Gly Asp Val
                245                 250                 255

Gln Ser Arg Val Ile Pro Ala Gly Asn Leu Tyr Ile Ser Gly Glu Lys
                260                 265                 270

Arg Arg Gly Glu Ala Asp Val Ala Glu Gly Ala Glu Ala Ile Met Gln
            275                 280                 285

Ala Met Ser Ala Cys Ala Pro Val Arg Asp Ile Arg Gly Glu Pro Gly
            290                 295                 300

Thr His Ala Gly Gly Met Leu Glu Arg Val Arg Lys Val Met Ala Ser
305                 310                 315                 320

Leu Thr Gly His Glu Met Ser Ala Ile Tyr Ile Gln Asp Leu Leu Ala
                325                 330                 335

Val Asp Thr Phe Ile Pro Arg Lys Val Gln Gly Gly Met Ala Gly Glu
                340                 345                 350

Cys Ala Met Glu Asn Ala Val Gly Met Ala Ala Met Val Lys Ala Asp
            355                 360                 365

Arg Leu Gln Met Gln Val Ile Ala Arg Glu Leu Ser Ala Arg Leu Gln
            370                 375                 380

Thr Glu Val Val Val Gly Gly Val Glu Ala Asn Met Ala Ile Ala Gly
385                 390                 395                 400

Ala Leu Thr Thr Pro Gly Cys Ala Ala Pro Leu Ala Ile Leu Asp Leu
                405                 410                 415

Gly Ala Gly Ser Thr Asp Ala Ala Ile Val Asn Ala Glu Gly Gln Ile
                420                 425                 430

Thr Ala Val His Leu Ala Gly Ala Gly Asn Met Val Ser Leu Leu Ile
```

```
            435                 440                 445
Lys Thr Glu Leu Gly Leu Glu Asp Leu Ser Leu Ala Glu Ala Ile Lys
    450                 455                 460

Lys Tyr Pro Leu Ala Lys Val Glu Ser Leu Phe Ser Ile Arg His Glu
465                 470                 475                 480

Asn Gly Ala Val Glu Phe Phe Arg Glu Ala Leu Ser Pro Ala Val Phe
                485                 490                 495

Ala Lys Val Val Tyr Ile Lys Glu Gly Glu Leu Val Pro Ile Asp Asn
                500                 505                 510

Ala Ser Pro Leu Glu Lys Ile Arg Leu Val Arg Arg Gln Ala Lys Glu
            515                 520                 525

Lys Val Phe Val Thr Asn Cys Leu Arg Ala Leu Arg Gln Val Ser Pro
    530                 535                 540

Gly Gly Ser Ile Arg Asp Ile Ala Phe Val Leu Val Gly Gly Ser
545                 550                 555                 560

Ser Leu Asp Phe Glu Ile Pro Gln Leu Ile Thr Glu Ala Leu Ser His
                565                 570                 575

Tyr Gly Val Val Ala Gly Gln Gly Asn Ile Arg Gly Thr Glu Gly Pro
                580                 585                 590

Arg Asn Ala Val Ala Thr Gly Leu Leu Leu Ala Gly Gln Ala Asn
    595                 600                 605

<210> SEQ ID NO 8
<211> LENGTH: 1824
<212> TYPE: DNA
<213> ORGANISM: Artificial Sequence
<220> FEATURE:
<223> OTHER INFORMATION: gdrA gene

<400> SEQUENCE: 8
atgccgttaa tagccgggat tgatatcggc aacgccacca ccgaggtggc gctggcgtcc      60
gacgacccgc aggcgagggc gtttgttgcc agcgggatcg tcgcgacgac gggcatgaaa     120
gggacgcggg acaatatcgc cggaccoctc gccgcgctgg agcaggccct ggcgaaaaca     180
ccgtggtcga tgagcgatgt ctctcgcatc tatcttaacg aagccgtgcc ggtgattggc     240
gatgtggcga tggagaccat caccgagacc attatcaccg aatcgaccat gatcggtcat     300
aacccgcaga cgccgggcgg ggtggcgtt gcgtgggga cgactatcgc cctcgggcgg     360
ctggcgacgc tgccggcggc gcagtatgcc gagggtgga tcgtactgat tgacgacgcc     420
gtcgatttcc ttgacgccgt gtggtggctc aatgaggcgc tcgaccgggg gatcaacgtg     480
gtggcggcga tcctcaaaaa ggacgacggc gtgctggtga caaccgcct gcgtaaaacc     540 ctgccggtgg tggatgaagt gacgctgctg agcaggtcc ccgaggggt aatggcggcg     600 gtggaagtgg ccgcgccggg ccaggttgtg cggatcctgt cgaatcccta cgggatcgcc     660
accttcttcg ggctaagccc ggaagagacc caggccatcg tccccatcgc ccgcgccctg     720
attggcaacc gttcagcggt ggtgctcaag accccgcagg gggatgtgca gtcgcgggtg     780
atcccggcgg gcaacctcta cattagcggc gaaaagcgcc gcggagaggc cgatgtcgcc     840
gagggcgcga aagccatcat gcaggcgatg agcgcctgcg ctccggtacg cgacatccgc     900
ggcgaaccgg gcacccacgc cggcggcatg cttgagcggg tgcgcaaggt aatggcgtcc     960
ctgaccggcc atgagatgag cgcgatatac atccaggatc tgctggcggt ggatacgttt    1020
attccgcgca aggtgcaggg cgggatgcc ggcgagtgcg ccatggagaa tgccgtcggg    1080
atggcggcga tggtgaaagc ggatcgtctg caaatgcagg ttatcgcccg cgaactgagc    1140
```

```
gcccgactgc agaccgaggt ggtggtgggc ggcgtggagg ccaacatggc catcgccggg    1200
gcgttaacca ctcccggctg tgcggcgccg ctggcgatcc tcgacctcgg cgccggctcg    1260
acggatgcgg cgatcgtcaa cgcggagggg cagataacgg cggtccatct cgccggggcg    1320
gggaatatgg tcagcctgtt gattaaaacc gagctgggcc tcgaggatct ttcgctggcg    1380
gaagcgataa aaagtaccc gctggccaaa gtggaaagcc tgttcagtat tcgtcacgag     1440
aatggcgcgt ggagttctt tcgggaagcc ctcagcccgg cggtgttcgc caaagtggtg    1500
tacatcaagg agggcgaact ggtgccgatc gataacgcca gcccgctgga aaaaattcgt    1560
ctcgtgcgcc ggcaggcgaa agagaaagtg tttgtcacca actgcctgcg cgcgctgcgc    1620
caggtctcac ccggcggttc cattcgcgat atcgcctttg tggtgctggt gggcggctca    1680
tcgctggact ttgagatccc gcagcttatc acggaagcct tgtcgcacta tggcgtggtc    1740
gccgggcagg gcaatattcg gggaacagaa gggccgcgca atgcggtcgc caccgggctg    1800
ctactggccg gtcaggcgaa ttaa                                            1824

<210> SEQ ID NO 9
<211> LENGTH: 117
<212> TYPE: PRT
<213> ORGANISM: Artificial Sequence
<220> FEATURE:
<223> OTHER INFORMATION: GdrB

<400> SEQUENCE: 9

Met Ser Leu Ser Pro Pro Gly Val Arg Leu Phe Tyr Asp Pro Arg Gly
1               5                   10                  15

His His Ala Gly Ala Ile Asn Glu Leu Cys Trp Gly Leu Glu Glu Gln
            20                  25                  30

Gly Val Pro Cys Gln Thr Ile Thr Tyr Asp Gly Gly Asp Ala Ala
        35                  40                  45

Ala Leu Gly Ala Leu Ala Ala Arg Ser Ser Pro Leu Arg Val Gly Ile
    50                  55                  60

Gly Leu Ser Ala Ala Gly Glu Ile Ala Leu Thr His Ala Gln Leu Pro
65                  70                  75                  80

Ala Asp Ala Pro Leu Ala Thr Gly His Val Thr Asp Ser Gly Asp His
                85                  90                  95

Leu Arg Thr Leu Gly Ala Asn Ala Gly Gln Leu Val Lys Val Leu Pro
            100                 105                 110

Leu Ser Glu Arg Asn
        115

<210> SEQ ID NO 10
<211> LENGTH: 354
<212> TYPE: DNA
<213> ORGANISM: Artificial Sequence
<220> FEATURE:
<223> OTHER INFORMATION: gdrB gene

<400> SEQUENCE: 10
atgtcgcttt caccgccagg cgtacgcctg ttttacgatc cgcgcgggca tcatgccggc     60
gccatcaatg agctgtgctg ggggctggag gagcaggggg tcccctgcca gaccataacc    120
tatgacggag cggtgacgc cgctgcgctg gcgccctgg cggccagaag ctcgcccctg      180
cgggtgggta tcgggctcag cgcagccggc gagatagccc tcactcatgc ccagctgccg    240
gcggacgcgc cgctggctac cggacacgtc accgatagcg cgatcatct gcgtacgctc     300
```
ggcgccaacg ccgggcagct ggttaaagtc ctgccgttaa gtgagagaaa ctga    354

<210> SEQ ID NO 11
<211> LENGTH: 462
<212> TYPE: PRT
<213> ORGANISM: Artificial Sequence
<220> FEATURE:
<223> OTHER INFORMATION: PduP from Klebsiella pneumoniae strain 1756

<400> SEQUENCE: 11

```
Met Asn Thr Ala Glu Leu Glu Thr Leu Ile Arg Thr Ile Leu Ser Glu
1               5                   10                  15

Lys Leu Ala Pro Thr Pro Pro Ala Pro Gln Gln Glu Gln Gly Ile Phe
            20                  25                  30

Cys Asp Val Gly Ser Ala Ile Asp Ala Ala His Gln Ala Phe Leu Arg
        35                  40                  45

Tyr Gln Gln Cys Pro Leu Lys Thr Arg Ser Ala Ile Ile Ser Ala Leu
    50                  55                  60

Arg Glu Thr Leu Ala Pro Glu Leu Ala Thr Leu Ala Glu Glu Ser Ala
65                  70                  75                  80

Thr Glu Thr Gly Met Gly Asn Lys Glu Asp Lys Tyr Leu Lys Asn Lys
                85                  90                  95

Ala Ala Leu Glu Asn Thr Pro Gly Ile Glu Asp Leu Thr Thr Ser Ala
            100                 105                 110

Leu Thr Gly Asp Gly Gly Met Val Leu Phe Glu Tyr Ser Pro Phe Gly
        115                 120                 125

Val Ile Gly Ala Val Ala Pro Ser Thr Asn Pro Thr Glu Thr Ile Ile
    130                 135                 140

Asn Asn Ser Ile Ser Met Leu Ala Ala Gly Asn Ser Val Tyr Phe Ser
145                 150                 155                 160

Pro His Pro Gly Ala Lys Lys Val Ser Leu Lys Leu Ile Ala Arg Ile
                165                 170                 175

Glu Glu Ile Ala Tyr Arg Cys Ser Gly Ile Arg Asn Leu Val Val Thr
            180                 185                 190

Val Ala Glu Pro Thr Phe Glu Ala Thr Gln Gln Met Met Ser His Pro
        195                 200                 205

Leu Ile Ala Val Leu Ala Ile Thr Gly Gly Pro Gly Ile Val Ala Met
    210                 215                 220

Gly Met Lys Ser Gly Lys Lys Val Ile Gly Ala Gly Ala Gly Asn Pro
225                 230                 235                 240

Pro Cys Ile Val Asp Glu Thr Ala Asp Leu Val Lys Ala Ala Glu Asp
                245                 250                 255

Ile Ile Ser Gly Ala Ala Phe Asp Tyr Asn Leu Pro Cys Ile Ala Glu
            260                 265                 270

Lys Ser Leu Ile Val Val Ala Ser Val Ala Asp Arg Leu Ile Gln Gln
        275                 280                 285

Met Gln Asp Phe Asp Ala Leu Leu Leu Ser Arg Gln Glu Ala Asp Thr
    290                 295                 300

Leu Arg Ala Val Cys Leu Pro Asp Gly Ala Ala Asn Lys Lys Leu Val
305                 310                 315                 320

Gly Lys Ser Pro Ala Ala Leu Leu Ala Ala Ala Gly Leu Ala Val Pro
                325                 330                 335

Pro Arg Pro Pro Arg Leu Leu Ile Ala Glu Val Glu Ala Asn Asp Pro
            340                 345                 350

Trp Val Thr Cys Glu Gln Leu Met Pro Val Leu Pro Ile Val Arg Val
```

```
                355                 360                 365
Ala Asp Phe Asp Ser Ala Leu Ala Leu Ala Leu Arg Val Glu Glu Gly
        370                 375                 380

Leu His His Thr Ala Ile Met His Ser Gln Asn Val Ser Arg Leu Asn
385                 390                 395                 400

Leu Ala Ala Arg Thr Leu Gln Thr Ser Ile Phe Val Lys Asn Gly Pro
                405                 410                 415

Ser Tyr Ala Gly Ile Gly Val Gly Gly Glu Gly Phe Thr Thr Phe Thr
            420                 425                 430

Ile Ala Thr Pro Thr Gly Glu Gly Thr Thr Ser Ala Arg Thr Phe Ala
                435                 440                 445

Arg Leu Arg Arg Cys Val Leu Thr Asn Gly Phe Ser Ile Arg
450                 455                 460

<210> SEQ ID NO 12
<211> LENGTH: 1386
<212> TYPE: DNA
<213> ORGANISM: Artificial Sequence
<220> FEATURE:
<223> OTHER INFORMATION: pduP gene from Klebsiella pneumoniae strain
      1756

<400> SEQUENCE: 12
atgaatacag cagaactgga aacccttatc cgcaccatcc tcagtgaaaa gctcgcgccg      60 acgcccctg cccctcagca agagcagggc attttctgcg atgtcggcag cgccatcgac     120
gccgctcatc aggcttttct ccgctatcag cagtgtccgc taaaaacccg cagcgccatt     180
atcagcgccc tgcgggagac gctggccccc gagctggcga cgttggcgga agagagcgcc     240
acggaaaccg gcatgggcaa caaagaagat aaatatctga aaataaagc cgctcttgaa      300 aatacgccgg gcatagagga tctcactacc agcgccctca ccggcgatgg cgggatggtg     360
ctgtttgagt actcgccgtt cggggttatt ggcgccgtgg cgcccagcac caacccaacg     420
gaaaccatta tcaacaacag tatcagcatg ctggcggcgg taacagcgt ctatttcagc      480 ccccatcccg cgcgaaaaa ggtctcgttg aagcttatcg ccaggatcga agagatcgcc      540
taccgctgca gcgggatccg taacctggtg gtgaccgttg ccgagccgac ctttgaagcc    600
acccagcaaa tgatgtccca cccgctgatt gccgttctgg ctatcaccgg tggccctggc     660
attgtggcga tgggcatgaa aagcggtaaa aaagtgatcg cgctggcgc cggcaatccg      720 ccgtgcatcg ttgatgaaac cgccgatctc gtcaaagccg ccgaagatat catcagcggc    780
gccgccttcg attacaacct gccctgtatc gccgaaaaaa gctgatcgt cgtcgcctcc     840 gtcgctgacc gcctgatcca gcagatgcag gattttgacg cgctgctgtt gagccgacag    900
gaggccgata ccctgcgtgc cgtctgcctg cccgacggcg cggcgaataa aaaactggtc    960
ggtaaaagcc cggctgcgct gctggcggcg gcgggtctcg ccgttccgcc tcgcccccct   1020
cgcctgctga tagccgaggt ggaggcgaac gaccccctgg gtgacctgcg agcagctgatg   1080 ccggtgctgc cgatcgtcag ggtcgccgac tttgacagcg ccctggcgct ggccctgcgc   1140
gttgaggagg gtctgcacca caccgccatt atgcactcgc agaatgtctc gcggctcaat   1200
ctggcggcac gcaccctgca gacctccatt tttgtcaaaa atggcccgtc ttacgcggga   1260
atcggcgtcg gcggcgaagg gtttaccacc ttcaccatcg ccacgccaac cggagaaggc    1320
accacctccg cgcggacgtt cgcccgcctg cggcgctgcg tgttgaccaa cggttttccc  1380
attcgc                                                               1386
```

```
<210> SEQ ID NO 13
<211> LENGTH: 589
<212> TYPE: PRT
<213> ORGANISM: Artificial Sequence
<220> FEATURE:
<223> OTHER INFORMATION: ReC from Cupriavidus necator

<400> SEQUENCE: 13
```

| | | | | | | | | | | | | | | |
|---|---|---|---|---|---|---|---|---|---|---|---|---|---|---|
| Met | Ala | Thr | Gly | Lys | Gly | Ala | Ala | Ser | Thr | Gln | Glu | Gly | Lys | Ser |
| 1 | | | | 5 | | | | | 10 | | | | | 15 |
| Gln | Pro | Phe | Lys | Val | Thr | Pro | Gly | Pro | Phe | Asp | Pro | Ala | Thr | Trp | Leu |
| | | | 20 | | | | | 25 | | | | | 30 | |
| Glu | Trp | Ser | Arg | Gln | Trp | Gln | Gly | Thr | Glu | Gly | Asn | Gly | His | Ala | Ala |
| | | | 35 | | | | | 40 | | | | | 45 | |
| Ala | Ser | Gly | Ile | Pro | Gly | Leu | Asp | Ala | Leu | Ala | Gly | Val | Lys | Ile | Ala |
| | 50 | | | | | 55 | | | | | 60 | | | | |
| Pro | Ala | Gln | Leu | Gly | Asp | Ile | Gln | Gln | Arg | Tyr | Met | Lys | Asp | Phe | Ser |
| 65 | | | | | 70 | | | | | 75 | | | | | 80 |
| Ala | Leu | Trp | Gln | Ala | Met | Ala | Glu | Gly | Lys | Ala | Glu | Ala | Thr | Gly | Pro |
| | | | | 85 | | | | | 90 | | | | | 95 | |
| Leu | His | Asp | Arg | Arg | Phe | Ala | Gly | Asp | Ala | Trp | Arg | Thr | Asn | Leu | Pro |
| | | | | 100 | | | | | 105 | | | | | 110 | |
| Tyr | Arg | Phe | Ala | Ala | Ala | Phe | Tyr | Leu | Leu | Asn | Ala | Arg | Ala | Leu | Thr |
| | | | 115 | | | | | 120 | | | | | 125 | | |
| Glu | Leu | Ala | Asp | Ala | Val | Glu | Ala | Asp | Ala | Lys | Thr | Arg | Gln | Arg | Ile |
| | 130 | | | | | 135 | | | | | 140 | | | | |
| Arg | Phe | Ala | Ile | Ser | Gln | Trp | Val | Asp | Ala | Met | Ser | Pro | Ala | Asn | Phe |
| 145 | | | | | 150 | | | | | 155 | | | | | 160 |
| Leu | Ala | Thr | Asn | Pro | Glu | Ala | Gln | Arg | Leu | Leu | Ile | Glu | Ser | Gly | Gly |
| | | | | 165 | | | | | 170 | | | | | 175 | |
| Glu | Ser | Leu | Arg | Ala | Gly | Val | Arg | Asn | Met | Met | Glu | Asp | Leu | Thr | Arg |
| | | | 180 | | | | | 185 | | | | | 190 | | |
| Gly | Lys | Ile | Ser | Gln | Thr | Asp | Glu | Ser | Ala | Phe | Glu | Val | Gly | Arg | Asn |
| | | 195 | | | | | 200 | | | | | 205 | | | |
| Val | Ala | Val | Thr | Glu | Gly | Ala | Val | Val | Phe | Glu | Asn | Glu | Tyr | Phe | Gln |
| | 210 | | | | | 215 | | | | | 220 | | | | |
| Leu | Leu | Gln | Tyr | Lys | Pro | Leu | Thr | Asp | Lys | Val | His | Ala | Arg | Pro | Leu |
| 225 | | | | | 230 | | | | | 235 | | | | | 240 |
| Leu | Met | Val | Pro | Pro | Cys | Ile | Asn | Lys | Tyr | Tyr | Ile | Leu | Asp | Leu | Gln |
| | | | | 245 | | | | | 250 | | | | | 255 | |
| Pro | Glu | Ser | Ser | Leu | Val | Arg | His | Val | Val | Glu | Gln | Gly | His | Thr | Val |
| | | | 260 | | | | | 265 | | | | | 270 | | |
| Phe | Leu | Val | Ser | Trp | Arg | Asn | Pro | Asp | Ala | Ser | Met | Ala | Gly | Ser | Thr |
| | | 275 | | | | | 280 | | | | | 285 | | | |
| Trp | Asp | Asp | Tyr | Ile | Glu | His | Ala | Ala | Ile | Arg | Ala | Ile | Glu | Val | Ala |
| | 290 | | | | | 295 | | | | | 300 | | | | |
| Arg | Asp | Ile | Ser | Gly | Gln | Asp | Lys | Ile | Asn | Val | Leu | Gly | Phe | Cys | Val |
| 305 | | | | | 310 | | | | | 315 | | | | | 320 |
| Gly | Gly | Thr | Ile | Val | Ser | Thr | Ala | Leu | Ala | Val | Leu | Ala | Ala | Arg | Gly |
| | | | | 325 | | | | | 330 | | | | | 335 | |
| Glu | His | Pro | Ala | Ala | Ser | Val | Thr | Leu | Leu | Thr | Thr | Leu | Leu | Asp | Phe |
| | | | 340 | | | | | 345 | | | | | 350 | | |
| Ala | Asp | Thr | Gly | Ile | Leu | Asp | Val | Phe | Val | Asp | Glu | Gly | His | Val | Gln |
| | | 355 | | | | | 360 | | | | | 365 | | | |

```
Leu Arg Glu Ala Thr Leu Gly Gly Gly Ala Gly Ala Pro Cys Ala Leu
    370                 375                 380

Leu Arg Gly Leu Glu Leu Ala Asn Thr Phe Ser Phe Leu Arg Pro Asn
385                 390                 395                 400

Asp Leu Val Trp Asn Tyr Val Val Asp Asn Tyr Leu Lys Gly Asn Thr
                405                 410                 415

Pro Val Pro Phe Asp Leu Leu Phe Trp Asn Gly Asp Ala Thr Asn Leu
            420                 425                 430

Pro Gly Pro Trp Tyr Cys Trp Tyr Leu Arg His Thr Tyr Leu Gln Asn
        435                 440                 445

Glu Leu Lys Val Pro Gly Lys Leu Thr Val Cys Gly Val Pro Val Asp
450                 455                 460

Leu Ala Ser Ile Asp Val Pro Thr Tyr Ile Tyr Gly Ser Arg Glu Asp
465                 470                 475                 480

His Ile Val Pro Trp Thr Ala Ala Tyr Ala Ser Thr Ala Leu Leu Ala
                485                 490                 495

Asn Lys Leu Arg Phe Val Leu Gly Ala Ser Gly His Ile Ala Gly Val
            500                 505                 510

Ile Asn Pro Pro Ala Lys Asn Lys Arg Ser His Trp Thr Asn Asp Ala
        515                 520                 525

Leu Pro Glu Ser Pro Gln Gln Trp Leu Ala Gly Ala Ile Glu His His
    530                 535                 540

Gly Ser Trp Trp Pro Asp Trp Thr Ala Trp Leu Ala Gly Gln Ala Gly
545                 550                 555                 560

Ala Lys Arg Ala Ala Pro Ala Asn Tyr Gly Asn Ala Arg Tyr Arg Ala
                565                 570                 575

Ile Glu Pro Ala Pro Gly Arg Tyr Val Lys Ala Lys Ala
            580                 585

<210> SEQ ID NO 14
<211> LENGTH: 1770
<212> TYPE: DNA
<213> ORGANISM: Artificial Sequence
<220> FEATURE:
<223> OTHER INFORMATION: reC gene from Cupriavidus necator

<400> SEQUENCE: 14
atggcgaccg gcaaaggcgc ggcagcttcc acgcaggaag gcaagtccca accattcaag      60
gtcacgccgg ggccattcga tccagccaca tggctggaat ggtcccgcca gtggcagggc     120
actgaaggca acggccacgc ggccgcgtcc ggcattccgg gcctggatgc gctggcaggc     180
gtcaagatcg cgccggcgca gctgggtgat atccagcagc gctacatgaa ggacttctca     240
gcgctgtggc aggccatggc cgagggcaag gccgaggcca ccgtccgct gcacgaccgg      300 cgcttcgccg gcgacgcatg gcgcaccaac ctcccatatc gcttcgctgc gcgttctac     360 ctgctcaatg cgcgcgcctt gaccgagctg gccgatgccg tcgaggccga tgccaagacc     420
cgccagcgca tccgcttcgc gatctcgcaa tgggtcgatg cgatgtcgcc cgccaacttc     480
cttgccacca atcccgaggc gcagcgcctg ctgatcgagt cgggcggcga atcgctgcgt     540
gccggcgtgc gcaacatgat ggaagacctg acacgcggca gatctcgca gaccgacgag      600 agcgcgtttg aggtcggccg caatgtcgcg gtgaccgaag cgccgtggt cttcgagaac      660 gagtacttcc agctgttgca gtacaagccg ctgaccgaca aggtgcacgc gcgccgctg      720 ctgatggtgc cgccgtgcat caacaagtac tacatcctgg acctgcagcc ggagagctcg     780
ctggtgcgcc atgtggtgga gcagggacat acggtgtttc tggtgtcgtg gcgcaatccg     840
```

```
gacgccagca tggccggcag cacctgggac gactacatcg agcacgcggc catccgcgcc    900
atcgaagtcg cgcgcgacat cagcggccag gacaagatca cgtgctcgg cttctgcgtg     960 ggcggcacca ttgtctcgac cgcgctggcg gtgctggccg cgcgcggcga gcacccggcc   1020
gccagcgtca cgctgctgac cacgctgctg gactttgccg acacgggcat cctcgacgtc   1080
tttgtcgacg agggccatgt gcagttgcgc gaggccacgc tgggcggcgg cgccggcgcg   1140
ccgtgcgcgc tgctgcgcgg ccttgagctg gccaatacct tctcgttctt gcgcccgaac   1200
gacctggtgt ggaactacgt ggtcgacaac tacctgaagg caacacgcc ggtgccgttc    1260 gacctgctgt tctggaacgg cgacgccacc aacctgccgg ggccgtggta ctgctggtac   1320
ctgcgccaca cctacctgca gaacgagctc aaggtaccgg gcaagctgac cgtgtgcggc   1380
gtgccggtgg acctgccag catcgacgtg ccgacctata tctacggctc gcgcgaagac    1440
catatcgtgc cgtggaccgc ggcctatgcc tcgaccgcgc tgctggcgaa caagctgcgc   1500
ttcgtgctgg gtgcgtcggg ccatatcgcc ggtgtgatca cccgccggc caagaacaag    1560 cgcagccact ggactaacga tgcgctgccg gagtcgccgc agcaatggct ggccggcgcc   1620
atcgagcatc acggcagctg gtggccggac tggaccgcat ggctgccgg gcaggccggc    1680 gcgaaacgcg ccgcgcccgc caactatggc aatgcgcgct atcgcgcaat cgaacccgcg   1740
cctgggcgat acgtcaaagc caaggcatga                                    1770
```

<210> SEQ ID NO 15
<211> LENGTH: 331
<212> TYPE: PRT
<213> ORGANISM: Artificial Sequence
<220> FEATURE:
<223> OTHER INFORMATION: LdhD from Pediococcus acidilactici

<400> SEQUENCE: 15

```
Met Lys Ile Ile Ala Tyr Gly Ile Arg Asp Asp Glu Lys Pro Tyr Leu
1               5                   10                  15

Asp Glu Trp Val Thr Lys Asn His Ile Glu Val Lys Ala Val Pro Asp
                20                  25                  30

Leu Leu Asp Ser Ser Asn Ile Asp Leu Ala Lys Asp Tyr Asp Gly Val
            35                  40                  45

Val Ala Tyr Gln Gln Lys Pro Tyr Thr Ala Asp Leu Phe Asp Lys Met
        50                  55                  60

His Glu Phe Gly Ile His Ala Phe Ser Leu Arg Asn Val Gly Leu Asp
65                  70                  75                  80

Asn Val Pro Ala Asp Ala Leu Lys Lys Asn Asp Ile Lys Ile Ser Asn
                85                  90                  95

Val Pro Ala Tyr Ser Pro Arg Ala Ile Ala Glu Leu Ser Val Thr Gln
            100                 105                 110

Leu Leu Ala Leu Leu Arg Lys Ile Pro Glu Phe Glu Tyr Lys Met Ala
        115                 120                 125

His Gly Asp Tyr Arg Trp Glu Pro Asp Ile Gly Leu Glu Leu Asn Gln
    130                 135                 140

Met Thr Val Gly Val Ile Gly Thr Gly Arg Ile Gly Arg Ala Ala Ile
145                 150                 155                 160

Asp Ile Phe Lys Pro Phe Gly Ala Lys Val Ile Ala Tyr Asp Val Phe
                165                 170                 175

Arg Asn Pro Ala Leu Glu Lys Glu Gly Met Tyr Val Asp Thr Leu Glu
            180                 185                 190
```

```
        Glu Leu Tyr Gln Gln Ala Asn Val Ile Thr Leu His Val Pro Ala Leu
                        195                 200                 205

Lys Asp Asn Tyr His Met Leu Asp Glu Lys Ala Phe Gly Gln Met Gln
            210                 215                 220

Asp Gly Thr Phe Ile Leu Asn Phe Ala Arg Gly Thr Leu Val Asp Thr
        225                 230                 235                 240

Pro Ala Leu Leu Lys Ala Leu Asp Ser Gly Lys Val Ala Gly Ala Ala
                        245                 250                 255

Leu Asp Thr Tyr Glu Asn Glu Val Gly Ile Phe Asp Val Asp His Gly
                        260                 265                 270

Asp Gln Pro Ile Asp Asp Pro Val Phe Asn Asp Leu Met Ser Arg Arg
                    275                 280                 285

Asn Val Met Ile Thr Pro His Ala Ala Phe Tyr Thr Arg Pro Ala Val
                        290                 295                 300

Lys Asn Met Val Gln Ile Ala Leu Asp Asn Asn Arg Asp Leu Ile Glu
        305                 310                 315                 320

Lys Asn Ser Ser Lys Asn Glu Val Lys Phe Glu
                        325                 330

<210> SEQ ID NO 16
<211> LENGTH: 996
<212> TYPE: DNA
<213> ORGANISM: Artificial Sequence
<220> FEATURE:
<223> OTHER INFORMATION: ldhD gene from Pediococcus acidilactici

<400> SEQUENCE: 16
atgaagatta ttgcttatgg aattcgtgac gatgaaaaac catatttaga cgaatgggta      60
acgaagaacc atatcgaggt taaagcggtc cccgatttgt tagattctag taacattgat     120
ttggcaaagg attacgatgg ggtagttgct taccaacaaa agccttacac cgctgattta     180
tttgataaga tgcacgaatt tgggattcat gccttctcgc tgcgtaacgt cggacttgat     240
aacgtacccg cagatgcact caagaaaaat gatatcaaaa tttcgaacgt accagcatat     300
tctccaagag caattgctga attgtcagtc acccaactgt tagcattact ccgtaagatt     360
cctgaatttg aatacaaaat ggctcatggc gattatcgtt gggaaccaga catcggtttg     420
gaacttaatc aaatgaccgt tggggtaatt ggtaccggac ggattggccg tgctgcaatt     480
gacattttta aaccatttgg cgcaaaggta attgcgtacg atgttttccg taatcctgca     540
ttagaaaagg aaggcatgta tgtagatact ttagaagagc tttaccaaca agctaacgtc     600
attactttac acgttccagc actaaaggat aattaccaca tgttggatga aaaggccttt     660
ggtcaaatgc aagacggaac cttcatccta aacttcgcgc ggggactttt agttgataca     720
cctgcacttt taaaggcgtt agatagtggt aaagttgctg gagctgcgct agatacttac     780
gaaaacgaag tcggcatctt tgatgtcgat catggtgatc aaccaattga tgacccagtt     840
tttaacgatt tgatgagtcg ccgtaacgta atgattacgc cacacgctgc cttctacacc     900
cgcccagcgg ttaaaaacat ggttcaaatc gccttagaca caaccgggga cttaattgaa     960
aagaattctt caaagaatga agttaagttt gagtaa                               996

<210> SEQ ID NO 17
<211> LENGTH: 1575
<212> TYPE: DNA
<213> ORGANISM: Artificial Sequence
<220> FEATURE:
<223> OTHER INFORMATION: Clostridium propionicum
<220> FEATURE:
```

```
<221> NAME/KEY: gene
<222> LOCATION: (1)..(1575)
<223> OTHER INFORMATION: popionyl-CoA transferase

<400> SEQUENCE: 17
atgagaaagg ttcccattat taccgcagat gaggctgcaa agcttattaa agacggtgat      60
acagttacaa caagtggttt cgttggaaat gcaatccctg aggctcttga tagagctgta     120
gaaaaaagat tcttagaaac aggcgaaccc aaaaacatta cctatgttta ttgtggttct     180
caaggtaaca gagacggaag aggtgctgag cactttgctc atgaaggcct tttaaaacgt     240
tacatcgctg tcactgggc tacagttcct gctttgggta aaatggctat ggaaaataaa     300
atggaagcat ataatgtatc tcagggtgca ttgtgtcatt tgttccgtga tatagcttct     360
cataagccag gcgtatttac aaaggtaggt atcggtactt tcattgaccc agaaatggc     420
ggcggtaaag taaatgatat taccaaagaa gatattgttg aattggtaga gattaaggg     480
caggaatatt tattctaccc tgcttttcct attcatgtag ctcttattcg tggtacttac     540
gctgatgaaa gcgaaaatat cacatttgag aaagaagttc tcctctgga aggaacttca     600
gtatgccagg ctgttaaaaa cagtggcggt atcgttgtag ttcaggttga aagagtagta     660
aaagctggta ctcttgaccc tcgtcatgta aaagttccag gaattatgt tgactatgtt     720
gttgttgctg acccagaaga tcatcagcaa tctttagatt gtgaatatga tcctgcatta     780
tcaggcgagc atagaagacc tgaagttgtt ggagaaccac ttcctttgag tgcaaagaaa     840
gttattggtc gtcgtggtgc cattgaatta gaaaaagatg ttgctgtaaa tttaggtgtt     900
ggtgcgcctc aatatgtagc aagtgttgct gatgaagaag gtatcgttga tttatgact     960
ttaactgctg aaagtggtgc tattggtggt gttcctgctg gtggcgttcg ctttggtgct    1020
tcttataatg cggatgcatt gatcgatcaa ggttatcaat tcgattacta tgatggcggc    1080
ggcttagacc tttgctattt aggcttagct gaatgcgatg aaaaaggcaa tatcaacgtt    1140
tcaagatttg gccctcgtat cgctggttgt ggtggtttca tcaacattac acagaataca    1200
cctaaggtat tcttctgtgg tactttcaca gcaggtggct aaaggttaa aattgaagat    1260
ggcaaggtta ttattgttca agaaggcaag cagaaaaaat tcttgaaagc tgttgagcag    1320
attacattca atggtgacgt tgcacttgct aataagcaac aagtaactta tattacagaa    1380
agatgcgtat tccttttgaa ggaagatggt ttgcacttat ctgaaattgc acctggtatt    1440
gatttgcaga cacagattct tgacgttatg gattttgcac ctattattga cagagatgca    1500
aacggccaaa tcaaattgat ggacgctgct ttgtttgcag aaggcttaat gggtctgaag    1560
gaaatgaagt cctaa                                                      1575

<210> SEQ ID NO 18
<211> LENGTH: 524
<212> TYPE: PRT
<213> ORGANISM: Artificial Sequence
<220> FEATURE:
<223> OTHER INFORMATION: Clostridium propionicum
<220> FEATURE:
<221> NAME/KEY: PEPTIDE
<222> LOCATION: (1)..(524)
<223> OTHER INFORMATION: propionyl-CoA transferase

<400> SEQUENCE: 18

Met Arg Lys Val Pro Ile Ile Thr Ala Asp Glu Ala Ala Lys Leu Ile
1               5                   10                  15

Lys Asp Gly Asp Thr Val Thr Thr Ser Gly Phe Val Gly Asn Ala Ile
            20                  25                  30
```

```
Pro Glu Ala Leu Asp Arg Ala Val Glu Lys Arg Phe Leu Glu Thr Gly
            35                  40                  45

Glu Pro Lys Asn Ile Thr Tyr Val Tyr Cys Gly Ser Gln Gly Asn Arg
    50                  55                  60

Asp Gly Arg Gly Ala Glu His Phe Ala His Glu Gly Leu Leu Lys Arg
65                  70                  75                  80

Tyr Ile Ala Gly His Trp Ala Thr Val Pro Ala Leu Gly Lys Met Ala
                85                  90                  95

Met Glu Asn Lys Met Glu Ala Tyr Asn Val Ser Gln Gly Ala Leu Cys
            100                 105                 110

His Leu Phe Arg Asp Ile Ala Ser His Lys Pro Gly Val Phe Thr Lys
        115                 120                 125

Val Gly Ile Gly Thr Phe Ile Asp Pro Arg Asn Gly Gly Lys Val
    130                 135                 140

Asn Asp Ile Thr Lys Glu Asp Ile Val Glu Leu Val Glu Ile Lys Gly
145                 150                 155                 160

Gln Glu Tyr Leu Phe Tyr Pro Ala Phe Pro Ile His Val Ala Leu Ile
                165                 170                 175

Arg Gly Thr Tyr Ala Asp Glu Ser Gly Asn Ile Thr Phe Glu Lys Glu
            180                 185                 190

Val Ala Pro Leu Glu Gly Thr Ser Val Cys Gln Ala Val Lys Asn Ser
        195                 200                 205

Gly Gly Ile Val Val Gln Val Glu Arg Val Val Lys Ala Gly Thr
    210                 215                 220

Leu Asp Pro Arg His Val Lys Val Pro Gly Ile Tyr Val Asp Tyr Val
225                 230                 235                 240

Val Val Ala Asp Pro Glu Asp His Gln Gln Ser Leu Asp Cys Glu Tyr
                245                 250                 255

Asp Pro Ala Leu Ser Gly Glu His Arg Arg Pro Glu Val Val Gly Glu
            260                 265                 270

Pro Leu Pro Leu Ser Ala Lys Lys Val Ile Gly Arg Gly Ala Ile
        275                 280                 285

Glu Leu Glu Lys Asp Val Ala Val Asn Leu Gly Val Gly Ala Pro Glu
    290                 295                 300

Tyr Val Ala Ser Val Ala Asp Glu Glu Gly Ile Val Asp Phe Met Thr
305                 310                 315                 320

Leu Thr Ala Glu Ser Gly Ala Ile Gly Gly Val Pro Ala Gly Gly Val
                325                 330                 335

Arg Phe Gly Ala Ser Tyr Asn Ala Asp Ala Leu Ile Asp Gln Gly Tyr
            340                 345                 350

Gln Phe Asp Tyr Tyr Asp Gly Gly Leu Asp Leu Cys Tyr Leu Gly
        355                 360                 365

Leu Ala Glu Cys Asp Glu Lys Gly Asn Ile Asn Val Ser Arg Phe Gly
370                 375                 380

Pro Arg Ile Ala Gly Cys Gly Gly Phe Ile Asn Ile Thr Gln Asn Thr
385                 390                 395                 400

Pro Lys Val Phe Phe Cys Gly Thr Phe Thr Ala Gly Gly Leu Lys Val
                405                 410                 415

Lys Ile Glu Asp Gly Lys Val Ile Ile Val Gln Glu Gly Lys Gln Lys
            420                 425                 430

Lys Phe Leu Lys Ala Val Glu Gln Ile Thr Phe Asn Gly Asp Val Ala
        435                 440                 445
```

```
Leu Ala Asn Lys Gln Gln Val Thr Tyr Ile Thr Glu Arg Cys Val Phe
    450                 455                 460
Leu Leu Lys Glu Asp Gly Leu His Leu Ser Glu Ile Ala Pro Gly Ile
465                 470                 475                 480
Asp Leu Gln Thr Gln Ile Leu Asp Val Met Asp Phe Ala Pro Ile Ile
                485                 490                 495
Asp Arg Asp Ala Asn Gly Gln Ile Lys Leu Met Asp Ala Ala Leu Phe
            500                 505                 510
Ala Glu Gly Leu Met Gly Leu Lys Glu Met Lys Ser
        515                 520

<210> SEQ ID NO 19
<211> LENGTH: 35
<212> TYPE: DNA
<213> ORGANISM: Artificial Sequence
<220> FEATURE:
<223> OTHER INFORMATION: J23101 promoter

<400> SEQUENCE: 19
tttacagcta gctcagtcct aggtattatg ctagc                               35

<210> SEQ ID NO 20
<211> LENGTH: 35
<212> TYPE: DNA
<213> ORGANISM: Artificial Sequence
<220> FEATURE:
<223> OTHER INFORMATION: J23108 promoter

<400> SEQUENCE: 20
ctgacagcta gctcagtcct aggtataatg ctagc                               35

<210> SEQ ID NO 21
<211> LENGTH: 328
<212> TYPE: DNA
<213> ORGANISM: Artificial Sequence
<220> FEATURE:
<223> OTHER INFORMATION: J23 promoter

<400> SEQUENCE: 21
tctagattta cagctagctc agtcctaggt attatgctag cggatcctgt aaaggagca     60 tctgacccat gggcagcagc catcaccatc atcaccacag ccagaattcg agctcggcgc   120
gcctgcaggt cgacaagctt gcggccgcat aatgcttaag tcgaacagaa agtaatcgta   180
ttgtacacgg ccgcataatc gaaatctgac agctagctca gtcctaggta taatgctagc   240
ggtacctgtt aaaggagcat ctgaccatat ggcagatctc aattggatat cggccggcca   300
cgcgatcgct gacgtcttcg aactcgag                                      328

<210> SEQ ID NO 22
<211> LENGTH: 29
<212> TYPE: DNA
<213> ORGANISM: Artificial Sequence
<220> FEATURE:
<223> OTHER INFORMATION: primer for J23

<400> SEQUENCE: 22
tactgaaccg ctctagattt acagctagc                                     29

<210> SEQ ID NO 23
<211> LENGTH: 29
<212> TYPE: DNA
<213> ORGANISM: Artificial Sequence
<220> FEATURE:
```

```
<223> OTHER INFORMATION: primer for J23

<400> SEQUENCE: 23
ctttaccaga ctcgagttcg aagacgtca                                      29

<210> SEQ ID NO 24
<211> LENGTH: 36
<212> TYPE: DNA
<213> ORGANISM: Artificial Sequence
<220> FEATURE:
<223> OTHER INFORMATION: primer

<400> SEQUENCE: 24
cagccagaat tcatgaaaag atcaaaacga tttgca                              36

<210> SEQ ID NO 25
<211> LENGTH: 40
<212> TYPE: DNA
<213> ORGANISM: Artificial Sequence
<220> FEATURE:
<223> OTHER INFORMATION: primer

<400> SEQUENCE: 25
ccctctaagc ttgatctccc actgaccaaa gctggccccg                          40

<210> SEQ ID NO 26
<211> LENGTH: 49
<212> TYPE: DNA
<213> ORGANISM: Artificial Sequence
<220> FEATURE:
<223> OTHER INFORMATION: primer

<400> SEQUENCE: 26
gagatcaagc ttagaggggg ccgtcatgtc gctttcaccg ccaggcgta                49

<210> SEQ ID NO 27
<211> LENGTH: 39
<212> TYPE: DNA
<213> ORGANISM: Artificial Sequence
<220> FEATURE:
<223> OTHER INFORMATION: primer

<400> SEQUENCE: 27
gttcgactta agtcagtttc tctcacttaa cggcaggac                           39

<210> SEQ ID NO 28
<211> LENGTH: 56
<212> TYPE: DNA
<213> ORGANISM: Artificial Sequence
<220> FEATURE:
<223> OTHER INFORMATION: primer for pduP

<400> SEQUENCE: 28
gctagcggta cctgttaaag gagcatctga caatgaatac agcagaactg gaaacc        56

<210> SEQ ID NO 29
<211> LENGTH: 36
<212> TYPE: DNA
<213> ORGANISM: Artificial Sequence
<220> FEATURE:
<223> OTHER INFORMATION: primer for pduP

<400> SEQUENCE: 29
ttaacacata tgttagcgaa tggaaaaacc gttggt                              36
```

```
<210> SEQ ID NO 30
<211> LENGTH: 49
<212> TYPE: DNA
<213> ORGANISM: Artificial Sequence
<220> FEATURE:
<223> OTHER INFORMATION: primer for reC GK

<400> SEQUENCE: 30
cgctaacata tgtgttaaag gagcatctga catggcgacc gataaaggc              49

<210> SEQ ID NO 31
<211> LENGTH: 39
<212> TYPE: DNA
<213> ORGANISM: Artificial Sequence
<220> FEATURE:
<223> OTHER INFORMATION: primer for reC GK

<400> SEQUENCE: 31
caattgagat cttcatgcct tggctttgac gtatcgccc                         39

<210> SEQ ID NO 32
<211> LENGTH: 30
<212> TYPE: DNA
<213> ORGANISM: Artificial Sequence
<220> FEATURE:
<223> OTHER INFORMATION: primer for ldhD

<400> SEQUENCE: 32
aataaaccat ggatgaaaat tattgcttat                                   30

<210> SEQ ID NO 33
<211> LENGTH: 30
<212> TYPE: DNA
<213> ORGANISM: Artificial Sequence
<220> FEATURE:
<223> OTHER INFORMATION: primer for ldhD

<400> SEQUENCE: 33
caagatctcg agttaatcaa atttgacctc                                   30

<210> SEQ ID NO 34
<211> LENGTH: 52
<212> TYPE: DNA
<213> ORGANISM: Artificial Sequence
<220> FEATURE:
<223> OTHER INFORMATION: primer for cppct540

<400> SEQUENCE: 34
aactcgagat cttgttaaag gagcatctga catgagaaag gttcccatta tt          52

<210> SEQ ID NO 35
<211> LENGTH: 30
<212> TYPE: DNA
<213> ORGANISM: Artificial Sequence
<220> FEATURE:
<223> OTHER INFORMATION: primer for cppct540

<400> SEQUENCE: 35
ccatatggta ccttaggact tcatttcctt                                   30

<210> SEQ ID NO 36
<211> LENGTH: 72
<212> TYPE: DNA
<213> ORGANISM: Artificial Sequence
<220> FEATURE:
<223> OTHER INFORMATION: oligomer for ldhA deletion
```

```
<400> SEQUENCE: 36
atcagcgtac ccgtgatgct aacttctctc tggaaggtct gaccggcttt aattaaccct      60
cactaaaggg cg                                                          72

<210> SEQ ID NO 37
<211> LENGTH: 73
<212> TYPE: DNA
<213> ORGANISM: Artificial Sequence
<220> FEATURE:
<223> OTHER INFORMATION: oligomer for ldhA deletion

<400> SEQUENCE: 37
acaccgattt taccggtacc gataacgcct gccgttttgc catacatagt taatacgact      60
cactataggg ctc                                                         73

<210> SEQ ID NO 38
<211> LENGTH: 57
<212> TYPE: DNA
<213> ORGANISM: Artificial Sequence
<220> FEATURE:
<223> OTHER INFORMATION: primer for ReC GK

<400> SEQUENCE: 38
cgctaattcg aatagtgacg gcagagagac aatcaaatca tggcgaccgg caaaggc         57

<210> SEQ ID NO 39
<211> LENGTH: 41
<212> TYPE: DNA
<213> ORGANISM: Artificial Sequence
<220> FEATURE:
<223> OTHER INFORMATION: primer for ReC GK

<400> SEQUENCE: 39
caattgcctg caggtcatgc cttggctttg acgtatcgcc c                          41

<210> SEQ ID NO 40
<211> LENGTH: 67
<212> TYPE: DNA
<213> ORGANISM: Artificial Sequence
<220> FEATURE:
<223> OTHER INFORMATION: primer for cppct540

<400> SEQUENCE: 40
caattgcctg caggcggata acaatttcac acaggaaaca gaattcatga gaaaggttcc      60
cattatt                                                                67

<210> SEQ ID NO 41
<211> LENGTH: 30
<212> TYPE: DNA
<213> ORGANISM: Artificial Sequence
<220> FEATURE:
<223> OTHER INFORMATION: primer for cppct540

<400> SEQUENCE: 41
ccatatcata tgttaggact tcatttcctt                                       30
```

POLY(3-HYDROXYPROPIONATE-B-LACTATE) BLOCK COPOLYMER USING MICROORGANISMS

CROSS-REFERENCE TO RELATED APPLICATION(S)

This application is a Divisional of U.S. patent application Ser. No. 16/754,480, filed on Apr. 8, 2020, now allowed, which is the U.S. National Phase application of International Application No. PCT/KR2019/002909, filed on Mar. 13, 2019, which claims the benefit of Korean Patent Application No. 10-2018-0030522, filed on Mar. 15, 2018, all of which are hereby incorporated by reference in their entirety for all purposes as if fully set forth herein.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file was created on May 2, 2022, is 48 kilobytes in size, and titled 29137.03094.US11_SEQ_LISTING_UPDATED.txt.

TECHNICAL FIELD

The present invention relates to a method for preparing a poly(3-hydroxypropionate-b-lactate) block copolymer, and more particularly to a method for preparing a poly(3-hydroxypropionate-b-lactate) block copolymer using recombinant microorganisms.

BACKGROUND

Polylactate (PLA), which is a representative biodegradable polymer having lactate as a monomer, is a polymer having high applicability to a general-purpose polymer or a medical polymer. Currently, PLA is being produced by polymerization of lactate produced from microorganism fermentation, but direct polymerization of lactate produces only PLA having a low molecular weight (1000 to 5000 Dalton). In order to synthesize PLA with at least 100,000 Dalton, there is a method of polymerizing PLA with higher molecular weight using a chain coupling agent from PLA having a low molecular weight obtained from direct polymerization of lactate. However, since this method uses the chain coupling agent, a process for preparing PLA with high molecular weight can be complicated due to addition of an organic solvent or the chain coupling agent, and it can be difficult to remove this organic solvent or chain coupling agent. Currently, in a commercialized process for producing PLA having a high molecular weight, a chemical synthesis method of converting lactate into lactide and then synthesizing the PLA through a ring opening condensation reaction of the lactide ring has been used.

However, such PLA has poor brittleness, and thus, to improve this, it has been reported that poly(3-hydroxypropionate-r-lactate) (P(3HP-r-LA)) random copolymer is developed by adding 3-hydroxypropionate (3HP) with good elongation. However, such poly(3-hydroxypropionate-r-lactate) has a problem that it is not crystallized and thus has poor physical properties.

Thus, in order to improve the problems of conventional polylactate and P(3HP-r-LA) random copolymer, the present inventors have biosynthesized a block copolymer [poly(3-hydroxypropionate-b-lactate)] from PLA and P(3HP) by culturing recombinant *E. coli* improved so as to be incapable of biosynthesizing lactic acid and transformed with PHA synthase genes. In addition, it was confirmed that such block copolymers significantly improve the problems such as brittleness which are problematic in conventional polylactate and P(3HP-r-LA) random copolymers, thereby embodying aspects of the present invention.

PRIOR ART LITERATURE

Patent Literature (Patent Literature 1) Korean Patent No. 10-0957773 (May 6, 2010)

Non-Patent Literature (Non-Patent Literature 1) Park, S. J., et al., Metabolic engineering of *Ralstonia eutropha*: for the biosynthesis of 2-hydroxyacid-containing polyhydroxyalkartoate, Metab. Eng. 20, 20-28 (2013)

DETAILED DESCRIPTION OF THE INVENTION

Technical Problem

It is an object of the present invention to provide a recombinant microorganism produced by a process in which recombinant microorganisms improved so as to be incapable of biosynthesizing lactic acid are transformed with a vector including a 3-hydroxypropionyl-CoA biosynthesis gene and a polyhydroxyalkanoate (PHA) synthetase gene, and a vector including a lactate biosynthesis gene and a gene of enzyme that converts lactate to lactyl-CoA.

It is another object of the present invention to provide a method for preparing a poly(3-hydroxypropionate-b-lactate) block copolymer by performing a two-step culture of the recombinant microorganism.

It is another object of the present invention to provide a composition for preparing a copolymer for the preparation of a poly(3-hydroxypropionate-b-lactate) block copolymer including the recombinant microorganism.

It is still another object of the present invention to provide a poly(3-hydroxypropionate-b-lactate) block copolymer prepared according to the above method.

Technical Solution

Hereinafter, the present invention will be described in more detail.

In order to achieve the above objects, one aspect of the present invention provides a method for preparing 3-hydroxypropionate-lactate block copolymer [P(3HP-b-LA)] comprising the following steps, and a 3-hydroxypropionate-lactate block copolymer produced by the above preparation method:

(a) a step of preparing a recombinant microorganism by transforming recombinant microorganisms improved so as to be incapable of biosynthesizing lactic acid with a vector including a 3-hydroxypropionyl-CoA biosynthesis gene and a polyhydroxyalkanoate (PHA) synthetase gene, and a vector including a lactate biosynthesis gene and a gene of enzyme that converts lactate to lactyl-CoA;

(b) a step of synthesizing P(3HP) by culturing the recombinant microorganism prepared in step (a) using a glycerol as a carbon source; and (c) a step of inhibiting P(3HP) production by adding IPTG and glucose, and biosynthesizing PLA at the end of P(3HP) synthesized in step (a) by enabling the expression of a lactate biosynthesis enzyme and an enzyme that converts lactate to lactyl-CoA.

Hereinafter, each step will be described in detail.

In step (a), first, in order to prepare a P(3HP-b-LA) block copolymer, recombinant microorganisms improved so as to be incapable of biosynthesizing lactic acid are transformed using a vector including a 3-hydroxypropionyl-CoA and polyhydroxyalkanoate (PHA) synthetase gene, and a vector including a lactate biosynthesis gene and a gene of enzyme that converts lactate to lactyl-CoA, thereby preparing a recombinant microorganism.

The recombinant microorganism improved so as to be incapable of biosynthesizing lactic acid may be knocked out so that lactate dehydrogenase (Ldh), for example, lactate dehydrogenase A (LdhA), inherent in the recombinant microorganism is inactivated.

The vector including a gene encoding 3-hydroxypropionyl-CoA biosynthesis-related enzyme and PHA synthetase, and the vector including a lactate biosynthesis gene-related enzyme gene and a gene of enzyme that converts lactate to lactyl-CoA may be prepared by a conventional method for preparing a gene recombinant vector, and may be introduced into microbial cells by a known method for preparing a transformed microorganism (for example, electroporation or the like).

The gene encoding 3-hydroxypropionyl-CoA biosynthesis-related enzymes may be preferably a gene encoding glycerol dehydratase (consisting of subunits of DhaB1 (SEQ ID NO: 1), DhaB2 (SEQ ID NO: 3) and DhaB3 (SEQ ID NO: 5)), glycerol dehydratase activase (consisting of GdrA (SEQ ID NO: 7) and subunits of GdrB (SEQ ID NO: 9)), CoA-dependent propionaldehyde dehydrogenase and aldehyde dehydrogenase.

Preferably, the gene encoding glycerol dehydratase (Accession No.: EC 4.2.1.30) may be dhaB123 (dhaB1 (SEQ ID NO: 2), dhaB2 (SEQ ID NO: 4), dhaB3 (SEQ ID NO: 6), glycerol dehydratase activase (Accession No.: EC 4.2.1.30) may be gdrAB (consisting of subunits of gdrA (SEQ ID NO: 8) and gdrB (SEQ ID NO: 10)), and the gene encoding CoA-dependent propionaldehyde dehydrogenase (Accession No.: EC 1.2.1.3; SEQ ID NO: 11) may be pduP (SEQ ID NO: 12).

The polyhydroxyalkanoate (PHA) synthase is an enzyme that biosynthesizes polyhydroxyalkanoate using CoA and hydroxy fatty acid thioesters as substrates, and may be a type of enzyme that uses fatty acids having 3-5 carbon atoms (for example, derived from various bacteria such as *Cupriavidus necator, Alcaligenes latus*) and a type of enzyme that uses fatty acids having 6-14 carbon atoms (for example, derived from *Pseudomonas* sp.).

For example, the PHA synthase and the gene encoding the same may be S506G and A510K amino acid substitution variants of the variant-encoding gene of PHA synthase ReC (SEQ ID NO: 13; Accession No.: EC 2.3.1.B2, gene reC; Genebank accession No. 105003.1, SEQ ID NO: 14) derived from *Cupriavidus necator* (*Ralstonia eutropha* H16), and a gene (reC_GK) encoding the same.

The lactate biosynthesis enzyme is an enzyme that biosynthesizes lactic acid from glucose, and examples thereof may be a gene (ldhA, ldhD (996 bp, Gene Accession No.: X70925.1, SEQ ID NO: 16)) encoding lactate dehydrogenase (Ldh) derived from *Pediococcus acidilactici*, for example, lactate dehydrogenase A (LdhA) or lactate dehydrogenase D (LdhD) (Accession No.: EC 1.1.1.28 (SEQ ID NO: 15).

When converting the lactate to lactyl-CoA, the enzyme may be, for example, propionyl-CoA transferase (pct). Propionyl-CoA transferase is an enzyme that catalyzes the chemical reaction of the following Chemical Scheme 1:

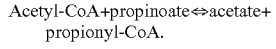
[Chemical Scheme 1]

The enzyme and the gene encoding the same may be derived from *Clostridium propionicum*.

For example, the propionyl-CoA transferase-encoding gene may include a base sequence selected from the group consisting of the following:

(a) a base sequence of SEQ ID NO: 17;

(b) a base sequence including A1200G mutation (means a mutation in which the 1200th base A is substituted with G; the same applies to the expression of the base sequence mutation described below) in a base sequence of SEQ ID NO: 17;

(c) a base sequence including T78C, T669C, A1125G and T1158C mutation in a base sequence of SEQ ID NO: 17;

(d) a base sequence encoding an amino acid sequence including A1200G mutation in the base sequence of SEQ ID NO: 17 and including G335A mutation (means a mutation in which the 355th amino acid Gly is substituted with Ala; the same applies to the expression of the amino acid sequence mutation described below) in an amino acid sequence corresponding to SEQ ID NO: 17;

(e) a base sequence encoding an amino acid sequence including A1200G mutation in a base sequence of SEQ ID NO: 17 and including A243T mutation in an amino acid sequence corresponding to SEQ ID NO: 17;

(f) a base sequence encoding an amino acid sequence including T669C, A1125G and T1158C mutations in a base sequence of SEQ ID NO: 1.7 and including D650 mutation in amino acid sequence corresponding to SEQ ID NO: 17;

(g) a base sequence encoding an amino acid sequence including A1200G mutation in a base sequence of SEQ ID NO: 17 and including D257N mutation in an amino acid sequence corresponding to SEQ ID NO: 17;

(h) a base sequence encoding an amino acid sequence including T669C, A1125G and T1158C mutations in a base sequence of SEQ ID NO: 17 and including D65N mutation in an amino acid sequence corresponding to SEQ ID NO: 17;

(i) a base sequence encoding an amino acid sequence including T669C, A1125G and T1158C mutations in a base sequence of SEQ ID NO: 17 and including T119I mutation in an amino acid sequence corresponding to SEQ ID NO: 17; and (j) a base sequence encoding an amino acid sequence including T78C, T669C, A1125G and T1158C mutations in a base sequence of SEQ ID NO: 17 and including V193A mutation in an amino acid sequence corresponding to SEQ ID NO: 17.

The propionyl-CoA transferase may include an amino acid sequence encoded by the base sequence.

Preferably, the gene may be cppct540 including a base sequence encoding an amino acid sequence including T78C, T669C, A1125G and T1158C mutations in a base sequence of SEQ ID NO: 17 and including V193A mutation in an amino acid sequence corresponding to SEQ ID NO: 17.

The enzymes can include additional mutations within a range that does not alter the activity of the molecule as a whole. For example, amino acid exchange in proteins and peptides that do not alter the activity of the molecule as a whole is known in the art. For example, commonly occurring exchanges include, but are not limited to, exchanges between amino acid residues Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu or Asp/Gly. In some cases, the protein may be modified by phosphorylation, sulfation, acrylation, glycosylation, methylation, farnesylation, or the like. In addition, include an enzyme protein having increased structural stability against heat, pH or the like of the protein or increased protein activity due to mutation Or modification on the amino acid sequence.

In addition, the gene encoding the enzyme may include nucleic acid molecules that contain functionally equivalent codons, or codons that encode the same amino acid (by the degeneracy of codons), or codons that encode biologically equivalent amino acids. The nucleic acid molecules may be isolated or produced using standard molecular biology techniques such as chemical synthesis methods or recombinant methods, or those that are commercially available can be used.

"Vector" means a gene construct including an essential regulatory element operably linked to express a gene insert encoding a target protein in a cell of an individual, and is a means for introducing a nucleic acid sequence encoding a target protein into a host cell. The vector may be at least one selected from the group consisting of various types of vectors including viral vectors such as plasmids, adenovirus vectors, retrovirus vectors and adeno-associated virus vectors, bacteriophage vectors, cosmid vectors, and YAC (Yeast Artificial Chromosome) vectors. In one example, the plasmid vector may be at least one selected from the group consisting of pBlue (e.g., pBluescript. II KS(+)), pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, and the like, the bacteriophage vector may be at least one selected from the group consisting of lambda gt4 lambda B, lambda-Charon, lambda Δz1, M13, and the like, and the viral vector may be SV40 or the like, but the present invention is not limited thereto.

The term "recombinant vector" includes cloning vectors and expression vectors containing foreign target genes. Cloning vector is a replicon, which includes an origin of replication, such as an origin of replication of a plasmid, phage or cosmid, to which another DNA fragment may be attached so as to bring about the replication of the attached fragment. Expression vectors have been developed so as to be used to synthesize proteins.

In the present specification, the vector is not particularly limited as long as it can express a desired enzyme gene in various host cells such as prokaryotic cells or eukaryotic cells and perform a function of preparing the gene. However, it is desirable that the gene inserted and transferred into the vector is irreversibly fused into the genome of the host cell so that gene expression in the cell persists stably for a long period of time.

Such vectors include transcriptional and translational expression control sequences that allow a target gene to be expressed within a selected host. An expression control sequence may include a promoter for performing transcription, any operator sequence for controlling such transcription, a sequence for encoding a suitable mRNA ribosomal binding site, and a sequence for controlling the termination of transcription and translation. For example, control sequences suitable for prokaryotes include a promoter, any operator sequence, and/or a ribosomal binding site. Control sequences suitable for eukaryotic cells include promoters, terminators and/or polyadenylation signals. The initiation codon and the termination codon are generally considered as a part of a nucleotide sequence encoding a target protein, and need to have actions in a subject when the gene construct is administered and be in frame with a coding sequence. A promoter of the vector may be constitutive or inducible. Further, in the case where the vector is a replicable expression vector, the vector may include a replication origin. In addition, enhancers, non-translated regions of the 5' and 3' ends of the gene of interest, selective markers (e.g., antibiotic resistance markers), or replicable units may be appropriately included. Vectors can be self-replicated or integrated into host genomic DNA.

Examples of useful expression control sequence may include early and late promoters of adenovirus, a monkey virus 40 (SV40) promoter, a mouse mammary tumor virus (MMTV) promoter, a human immunodeficiency virus (HIV) such as a long terminal repeat (LTR) promoter of HIV, molonivirus, cytomegalovirus (CMV) promoter, epstein barr virus (EBV) promoter, and rous sarcoma virus (RSV) promoter, RNA polymerase II promoter, β-actin promoter, human heroglobin promoter and human muscle creatine promoter, lac system, trp system, TAC or TRC system, T3 and T7 promoters, a major operator and promoter site of a phage lambda, a regulatory site of a fd coat protein, promoters for phosphoglycerate kinase (PGK) or other glycol degrading enzyme, phosphatase promoters, such as a promoter of yeast acid phosphatase such as Pho5, a promoter of a yeast alpha-mating factor, and other sequences known to regulate gene expression of prokaryotic or eukaryotic cells and their viruses and combinations thereof.

In order to increase the expression level of a transformed gene in a cell, the target gene and transcription and translation expression control sequences should be operably linked to each other. Generally, the term "operably linked" means that the DNA sequences being linked are contiguous, and, in the case of a secretory leader, contiguous and present in a reading frame. For example, DNA for a pre-sequence or a secretory leader is operably linked to DNA encoding polypeptide when expressed as pre-protein participating in secretion of protein, a promoter or an enhancer is operably linked to a coding sequence when affecting the transcription of the sequence; or a ribosomal binding site is operably linked to a coding sequence when affecting the transcription of the sequence, or a ribosomal binding site is operably linked to a coding sequence when arranged to facilitate translation. The linkage between these sequences is performed by ligation at a convenient restriction enzyme site. However, when the site does not exist, the linkage may be performed using a synthetic oligonucleotide adaptor or a linker according to a conventional method.

Those skilled in the art may appropriately select from among various vectors, expression control sequences, hosts and the like suitable for the present invention, taking into account the nature of the host cell, the copy number of the vector, the ability to regulate the copy number and the expression of other protein encoded by the corresponding vector (e.g., the expression of an antibiotic marker).

The recombinant microorganism provided herein can be obtained by transforming a host microorganism cell using the above recombinant vector.

As used herein, the term "transformation" means that a target gene is introduced into a host microorganism and thereby, the target gene can be replicated as a factor outside of chromosome or by means of completion of the entire chromosome.

The microorganism that can be used as the host microorganism may be selected from the group consisting of prokaryotic cells and eukaryotic cells. In general, microorganisms having high introduction efficiency of DNA and high expression efficiency of the introduced DNA may be used as the host microorganism. Specific examples of host microorganisms include known prokaryotic and eukaryotic hosts such as *Escherichia* sp. including *E. coli* (for example, *E. coli* DH5a, *E. coli* JM101, *E. coli* K12, *E. coli* W3110, *E. coli* X1776, *E. coli* B and *E. coli* XL1-Blue), *Pseudomonas* sp., *Bacillus* sp., *Streptomyces* sp., *Erwinia* sp., *Serratia* sp., *Providencia* sp., *Corynebacterium* sp., *Leptospira* sp., *Salmonella* sp., *Brevibacterium* sp., *Hypomonas* sp., *Chromobacterium* sp., *Nocadia* sp., fungi or yeast, but are not limited thereto. Once transformed into a suitable host, the vector may replicate and function independently of the host genome, or may in some instances, integrate into the genome itself.

In addition, for the purposes of the present invention, the host cell may be a microorganism having a pathway that biosynthesizes hydroxyacyl-CoA from a carbon source.

As the transformation method, suitable standard techniques as known in the art, such as electroporation, electroinjection, microinjection, calcium phosphate co-precipitation, calcium chloride/rubidium chloride method, retroviral infection, DEAE-dextran, cationic liposome method, polyethylene glycol-mediated uptake, gene guns and the like may be used, but are not limited thereto. At this time, the vector may be introduced in the form of a linearized vector by digestion of a circular vector with suitable restriction enzymes.

Step (b) is a step of synthesizing P(3HP) by culturing the recombinant microorganism. Specifically, it is characterized in that the recombinant microorganism is cultured in a medium containing glycerol as a carbon source to biosynthesize only P(3HP). The medium and culture conditions used at this time can be appropriately selected from those normally used according to the type of the recombinant microorganism. At the time of culture, conditions such as temperature, pH of the medium and culture time can be appropriately adjusted so as to be compatible with the growth of cells and the Preparation of the copolymer. Examples of the culture method include, but are not limited to, a batch mode, a continuous mode and a fed-batch mode.

In addition, the medium used for the cultivation must adequately satisfy the requirements for cultivation of a specific strain. The medium may include various carbon sources, nitrogen sources, phosphorus sources and trace element components. However, the first-step culture is characterized by including glycerol as a carbon source and not including glucose for the Preparation of P(3HP) as a carbon source in the medium.

The nitrogen source in the medium may include, but are not limited to, peptone, yeast extract, meat extract, malt extract, corn steep liquid, soybean meal, and urea, or an inorganic compound such as ammonium sulfate, ammonium chloride, ammonium phosphate, ammonium carbonate and ammonium nitrate. Nitrogen sources can also be used individually or as a mixture. The phosphorus source in the medium may include, but are not limited to, potassium dihydrogen phosphate or dipotassium hydrogen phosphate or a corresponding sodium-containing salt. Further, the culture medium may include, but not limited to, metal salts such as magnesium sulfate or ferric sulfate that are necessary for growth, or essential growth materials such as amino acids and vitamins. The above-mentioned materials may be added to the culture in an appropriate manner by batch culture or continuous culture during the cultivation process.

In addition, if necessary, the pH of the culture may be adjusted using basic compounds such as sodium hydroxide, potassium hydroxide, and ammonia, or acid compounds such as phosphoric acid and sulfuric acid, in an appropriate manner. Moreover, the generation of air bubbles may be prevented using an antifoaming agent such as fatty acid polyglycol ester. To maintain aerobic conditions, oxygen or an oxygen-containing gas (e.g., air) is injected into the culture. The temperature of the culture media may usually be in a range of 20° C. to 45° C., preferably 25° C. to 40° C. The cultivation may be continued until the polymer production reaches its maximum level.

Further, step (c) is characterized in that after the first-step culture, a lactate-producing enzyme and a lactyl-coA converting enzyme are expressed through IPTG induction and then PLA may be biosynthesized by further including glucose as a carbon source. The IPTG induction means that isopropyl β-D-1-thiogalactopyranoside (also known as IPTG, or lacY) triggers transcription of the lac operon to induce protein expression where the gene is under the control of the lac operon. Preferably, IPTG is used in an amount of 0.1 to 1.0 mM, more preferably 0.5 mM, and induction may be preferably performed about 8 to 24 hours (1 day) after the start of the culture.

In this way, when a lactate-producing enzyme and a lactyl-coA converting enzyme are expressed through IPTG induction and then glucose is further added as a carbon source to the culture solution, the use of glycerol is interrupted by a carbon catabolic repression system in which *E. coli* selectively introduces only glucose into the cell, and PLA is biosynthesized at the P(3HP) end where biosynthesis is interrupted, thereby preparing a P(3HP-b-LA) block copolymer. The culture conditions in step (c) can be appropriately adjusted similarly to step (b). Preferably, the first-step and second-step cultures of steps (b) and (c) can be carried out for 2 to 7 days, more preferably for about 4 days.

Through steps (b) and (c), the recombinant microorganism prepared in step (a) does not express a gene encoding a lactate biosynthetic enzyme and a gene encoding a lactyl-coA converting enzyme from the initial culture according to the present invention, but expresses a gene encoding the enzymes related to 3-hydroxypropionyl-CoA biosynthesis and PHA synthase genes by using glycerol as a carbon source and a P(3HP) synthase gene, so that P(3HP) is biosynthesized in the first-step culture. Subsequently, when glucose is supplied as a carbon source, the use of glycerol is interrupted by the carbon catabolic repression system, thereby inhibiting P(3HP) production. When IPTG is added together with glucose, the gene encoding a lactate biosynthetic enzyme and the gene encoding a lactyl-coA converting enzyme are expressed by the IPTG induction system in the second-step culture. Therefore, PLA is biosynthesized at the P(3HP) end, and P(3HP-b-LA) is biosynthesized.

The method for preparing P(3HP-b-LA) block copolymer provided by the present invention may, after culturing the recombinant microorganism, further include collecting (or isolating or purifying) the produced P(3HP-b-LA) block copolymer from the culture.

The P(3HP-b-LA) block copolymer produced from recombinant microorganism can be isolated from cells or culture media by methods well known in the art. Examples of the method for recovering P(3HP-b-LA) block copolymers include methods such as centrifugation, ultrasonic crushing, filtration, ion exchange chromatography, high performance liquid chromatography (HPLC), gas chromatography (GC) and the like, but are not limited thereto.

The P(3HP-b-LA) block copolymer produced by the above preparation method may contain 10 mol % or more of lactate (the upper limit is not particularly limited, but may be about 90 mol % or less, but is not limited thereto).

BRIEF DESCRIPTION OF THE DRAWINGS

FIG. 1 is a diagram showing a preparation method and a cleavage map of pCDFJ23 vector.

FIG. 2 is a diagram showing a preparation method and a cleavage map of pCDFJ23-dhaB123-gdrAB-pduP-reC_GK.

FIG. 3 is a diagram showing a preparation method and a cleavage map of pTrcHisB-ldhD-CPPCT540.

FIG. 4 is a graph showing the results of DSC analysis of the P(3HP-h-LA) block copolymer according to the present invention.

FIG. 5 is a graph showing the results of DSC analysis of P(3HP-r-LA) random copolymer.

FIG. 6 is a diagram showing a preparation method and a cleavage map of pBlue-re_GK-CPPCT540 vector for the preparation of a P(3HP-r-LA) random copolymer.

DETAILED DESCRIPTION OF THE EMBODIMENTS

Hereinafter, preferred embodiments of the present invention will be described in more detail to facilitate understanding of the invention. However, these examples are presented for illustrative purposes only and are not intended to limit the scope of the present invention.

Example 1. Preparation of Recombinant Vector for Preparation of 3-Hydroxypropionate-Lactate Block Copolymer All DNA cloning experiments were performed according to standard methods (see J. Sambrook, E. F. Fritsch, T. Maniatis, Molecular Cloning. A laboratory Manual, 2 nd Ed. Cold Spring Harbor Laboratory Press, Cold Spring Harbor, New York, 1989).

1-1. Preparation of pCDFJ23-dhaB123-gdrAB-pduP-reC_GK Recombinant Vector pCDFduet™-1 (Novagen, USA, 3.7 kb) contains two T7 promoters whose expression is induced by IPTG. In this experiment, this was deleted and two constantly expressed promoters were inserted. DNA fragment of pCDFduet™-1 was digested with XbaI/XhoI, and DNA fragments containing the sequences of J23101 (SEQ ID NO: 19) and J23108 promoter (SEQ ID NO: 20) that were constantly expressed were inserted into the XbaI/XhoI recognition site. The size of the inserted DNA fragment (promoter) containing the sequences of the J23101 and J23108 promoters was 328 bp (SEQ ID NO: 21). For insertion of the J23101 and J23108 promoters, primers having XbaI/XhoI recognition sites [5'-TACTGAACCGCTCTAGATTTACAGCTAGC-3'(SEQ ID NO: 22) and 5'-CTTTACCAGACTCGAGTTCGAAGACGTCA-3'(SEQ ID NO: 23)] were used. The preparation method of the pCDFJ23 vector is shown in FIG. 1.

Meanwhile, in order to isolate glycerol dehydratase (DhaB), glycerol dehydratase reactivase (PduAB) and. CoA-dependent propionaldehyde (PduP) genes, the total DNA of *Klebsiella pneumoniae* DSM 2026 was extracted, primers [5'-cagcca gaattcatgaaaagatcaaaacgatttgca-3'(SEQ ID NO: 24) and 5'-ccctct aagctt gatctcccactgac-caaagctggccccg-3'(SEQ ID NO: 25)] were prepared. PCR was performed at one time using the extracted total DNA as a template, and then a 4.7 kb gene fragment corresponding to dhaB1, dhaB2, dhaB3 and gdrA genes was identified. Gene fragments formed as a result of PCR were isolated using 1% agarose gel and purified using Wizard DNA purification kit. The purified gene fragment was treated with restriction enzymes EcoRI and HindIII, and then mixed with the pCDFJ23 vector fragment, to which T4 DNA ligase (available from Takara) was added, allowed to react at 4° C., and inserted into EcoRI/HindIII recognition site. Thereby, 7 kb of pCDFJ23-dhaB123-gdrAB recombinant plasmid was prepared.

In addition, in order to isolate Glycerol dehydratase reactivase (GdrB) gene, the total DNA of *Klebsiella pneumoniae* DSM 2026 was extracted and primers [5'-gagatc aagctt agagggggccgtcatgtcgattcaccgccaggcgta-3'(SEQ ID NO: 26) and 5'-gttcga cttaag tcagtactctcacttaacggcaggac-3' (SEQ ID NO: 27)] were prepared. PCR was performed using the extracted total DNA as a template, and then a 0.3 kb gene fragment corresponding to gdrB gene was identified. Gene fragments formed as a result of PCR were isolated using 1% agarose gel and purified using Wizard DNA purification kit. The purified gene fragment was treated with restriction enzymes HindIII and AflII, and then mixed with the pCDFJ23-dhaB123-gdrA recombinant plasmid fragment, to which T4 DNA ligase (available from Takara) was added, allowed to react at 4° C., and inserted into the HindIII/AflII recognition site. Thereby, 7.3 kb of pCDFJ23-dhaB123-gdrAB recombinant plasmid was prepared.

Furthermore, in order to isolate CoA-dependent propionaldehyde (PduP) gene, the total DNA of *Klebsiella pneumoniae* DSM 2026 was extracted and primers [(5'-gctagc ggtacc tgttaaaggagcatctgacaatgaatacagcagaactggaaacc-3' (SEQ ID NO: 28) and 5'-ttaaca catatg ttagcgaatg-gaaaaaccgttggt-3' (SEQ ID NO: 29))] were prepared. PCR was performed at one time using the extracted total DNA as a template, and a 1.4 kb gene fragment corresponding to pduP gene was identified. Gene fragments formed as a result of PCR were isolated using 1% agarose gel and purified using Wizard DNA purification kit. The purified gene fragment was treated with restriction enzymes KpnI and NdeI, and then mixed with the pCDFJ23-dhaB123-gdrAB recombinant plasmid fragment, to which T4 DNA ligase (available from Takara) was added and allowed to react at 4° C. Thereby, 8.7 kb of pCDFJ23-dhaB123-gdrAB-pduP recombinant plasmid was prepared.

And, in order to amplify the gene fragment corresponding to reC_GK which is a variant (S506G. A510K) gene of *Cupriavidus necator* (*Ralstonia eutropha*) PHA synthase, PCR was performed using primers [(5'-cgctaa catatg tgt-taaaggagcatctgacatggcgaccgataaaggc-3' (SEQ ID NO: 30) and 5'-caattg agatct tcatgccttggctttgacgtatcgccc-3' (SEQ ID NO: 31)], the amplified 1.8 kb gene fragment was treated with NdeI/BglII restriction enzyme, then mixed with the pCDFJ23-dhaB123-gdrAB-pduP recombinant plasmid fragment, to which T4 DNA ligase (available from Takara) was added, allowed to react at 4° C. and inserted into the NdeI/BglII recognition site. Thereby, 10.5 kb of pCDFJ23-dhaB123-gdrAB-pduP-reC_GK recombinant vector was finally prepared. The preparation method and cleavage map of such pCDFJ23-dhaB123-gdrAB-pduP-reC_GK recombinant vector are shown in FIG. 2.

1-2. Preparation of pTrcHisB-ldhD-cppct540 Recombinant Vector

A propionyl-CoA transferase (CP-PCT) variant derived from *Clostridium propionicum* was used as a propionyl-CoA transferase gene (pet), and a gene derived from *Pediococcus acidilactici* was used as a lactate dehydrogenase gene. The vector used at this time was pTricHisB (Invitrogen Co., USA) containing a Trc promoter which is an IPTG induction system.

First, in order to isolate a lactate dehydrogenase gene, the total DNA of *Pediococcus acidilactici* was extracted, primers [5'-aataaa ccatgg atgaaaattattgcttat-3'(SEQ ID NO: 32) and 5'-caagat ctcgag ttaatcaaatttgacctc-3'(SEQ ID NO: 33)] were prepared and PCR was performed using the extracted total DNA as a template. The obtained PCR product was electrophoresed to confirm a 1 kb gene fragment corresponding to a ldhD gene, and the gene was obtained. Gene fragments formed as a result of PCR were isolated using 1% agarose gel and purified using Wizard DNA purification kit. The purified gene fragment was treated with restriction enzymes NcoI and XhoI, and then mixed with the pTricHisB, to which T4 DNA ligase (available from Takara) was added and allowed to react at 4° C. Thereby, 5.4 kb of pTrcHisB-ldhD recombinant plasmid was prepared.

Then, in order to construct an operon-type system so that the propionyl-CoA transferase was expressed under the influence of the Trc promoter, *Clostridium propionicum*-derived propionyl-CoA transferase (CP-PCT) variant (CP-PCT Variant 540; including Val193Ala and silent mutations T78C, T669C, A1125G, T1158C) were used. The selection method of CP-PCT 540 is described in detail in Korean Patent Application No. 10-2018-002497, which is incorporated herein by reference. CP-PCT Variant 540 (including Val 193Ala and silent mutations T78C, T669C, A1125G, T1158C) selected in this way was subjected to PCK using primers [5'-aactcg agatct tgttaaaggagcatctgac atgagaaaggacccattatt-3'(SEQ ID NO: 34) and 5'-ccatat ggtacc ttaggacttcatacctt-3'(SEQ ID NO: 35)] to obtain a L5 kb amplified gene fragment. This was treated with restriction enzyme BglII/KpnI, and then mixed with the pTrcHisB-ldhD recombinant plasmid, to which T4 DNA ligase (available from Takara) was added and allowed to react at 4° C. to prepare 6.9 kb of pTrcHisB-ldhD-CPPCT 540 recombinant plasmid. The preparation method and cleavage map of the pTrcHisB-ldhD-CPPCT 540 recombinant vector are shown in FIG. 3.

Example 2. Preparation of Recombinant Strain for Preparation of 3-Hydroxypropionate-Lactate Block Copolymer 2.1. Preparation of ldhA Gene Knockout Variants In order to prepare a lactate free polymer based on *Escherichia coli* XL1-Blue (Stratagene, USA), *Escherichia coli* XL1-blue-derived D-lactate dehydrogenase gene (ldhA; fermentative D-lactate dehydrogenase, NAD-dependent [*Escherichia coli* str. K-12 substr.] Gene accession number: NC_000913.3, enzyme accession number: EC_1.1.1.28), involving in the preparation of lactate during the metabolic process of *Escherichia coli*, was knocked out from genomic DNA to prepare *Escherichia coli* variant, *E. coli* XL1-Blue (Δ ldhA) having deletion in ldhA was prepared. Deletion of the gene was performed using a red-recombination method well known in the art. The oligomer used to delete ldhA was synthesized by the base sequence of SEQ ID NO: 36 (5'-atcagcgtacccgtgatgctaacttctctctggaaggtctgaccggctttaat-taaccctcactaaagggcg-3') and SEQ ID NO: 37 (5'-acaccgat-tttaccggtaccgataacgcctgccgttttgccatacatagttaatacgactcac-tataggctc-3')

2.2, Preparation of Recombinant Strain for Preparation of 3-Hydroxypropionate-Lactate Block Copolymer The *Escherichia coli* mutant having deletions in ldhA, *E. coli* XL1-Blue (ΔldhA), prepared in Example 2.1 was transformed by electroporation using the recombinant vectors pCDFJ23-dhaB123-gdrAB-pduP-reC_GK and pTrcHisB-ldhD-CPPCT 540 prepared in Examples 1.1 and 1.2 to prepare a recombinant strain for the preparation of the P(LA-b-3HP) block copolymer.

Example 3. Preparation of 3-Hydroxypropionate-Lactate Block Copolymer Using IPTG Induction The recombinant strain prepared in Example 2.2 was cultured in two-steps as follows to obtain a 3-hydroxypropionate-lactate block copolymer.

First, for the first-step culture, the transformed recombinant *E. coli* prepared in Example 2.2 was inoculated into 100 ml MR medium further containing 100 mg/L of ampicillin, 25 mg/L of streptomycin, 20 g/L of glycerol, 0.5 mM of vitamin 1312 and 10 mg/L of thiamine ($KH_2PO_4$ 6.67 g, $(NH_4)_2HPO_4$ 4 g, $MgSO_4 \cdot 7H_2O$ 0.8 g, citric acid 0.8 g, and trace metal solution 5 mL per 1 L of medium; wherein the trace metal solution contains 5M HCl 5 mL, $FeSO_4 \cdot 7H_2O$ 10 g, $CaCl_2$ 2 g, $ZnSO_4 \cdot 7H_2O$ 2.2 g, $MnSO_4 \cdot 4H_2O$ 0.5 g, $CuSO_4 \cdot 5H_2O$ 1 g, $(NH_4)_6Mo_7O_2 \cdot 4H_2O$ 0.1 g, and $Na_2B_4O_2 \cdot 10H_2O$ 0.02 g per 1 L) and cultured with stirring at 30° C. and 250 rpm.

After 1 day from the start of the culture, isopropyl β-D-1-thiogalactopyranoside (IPTG) was added at 0.5 mM so that the IPTG induction system was used in 100 ml of the culture, and 10 g/L of glucose was added to perform IPTG induction. Thereby, the LA biosynthetic enzyme and the LA-CoA-converting enzyme were expressed, and the use of glycerol was interrupted and the Preparation of P(3HP) was inhibited, resulting in PLA biosynthesis at the interrupted P(3HP) end.

Subsequently, the induced culture solution was further cultured (second-sep culture) for 3 days.

Comparative Example 1. Preparation of 3-Hydroxypropionate Polymer without IPTG Induction In order to compare with the preparation method according to the present invention, 3-hydroxypropionate polymer was produced in one-step culture without using IPTG induction. Specifically, in a separate flask, the transformed recombinant *E. coli* prepared in Example 2.2 was inoculated in 100 ml MR medium further containing 100 mg/L of ampicillin, 25 mg/L of streptomycin, 20 g/L of glycerol and 0.5 mM of vitamin B12 ($KH_2PO_4$ 6.67 g, $(NH_4)2HPO_4$ 4 g, $MgSO_4 \cdot 7H_2O$ 0.8 g, citric acid 0.8 g, and trace metal solution 5 mL per 1 L of medium; wherein the trace metal solution contains 5M HCl 5 mL, $FeSO_4 \cdot 7H_2O$ 10 g, $CaCl_2$ 2 g, $ZnSO_4 \cdot 7H_2O$ 2.2 g, $MnSO_4 \cdot 4H_2O$ 0.5 g, $CuSO_4 \cdot 5H_2O$ 1 g, $(NH_4)6Mo_7O_2 \cdot 4H_2O$ 0.1 g, and $Na_2B_4O_2 \cdot 10H_2O$ 0.02 g per 1 L) and cultured for a total of 4 days while stirring at 250 rpm at 30° C.

Experimental Example 1. Analysis of Molecular Weight and Composition of the Prepared Polymer The culture solution subjected to the IPTG induction according to Example 3, and the culture solution not subjected to the IPTG induction according to Comparative Example 1 were respectively centrifuged at 4° C. and 4000 rpm for 10 minutes to collect microbial cells, washed twice with a sufficient amount of distilled water and then dried at 80° C. for 12 hours. In order to confirm the polymer content and composition in the dried microbial cells, GC analysis was performed. For this purpose, the microbial cells from which moisture was removed were quantified and then reacted with methanol under a sulfuric acid catalyst using chloroform as a solvent at 100° C. This was mixed by adding distilled water in an amount equivalent to a half of chloroform at room temperature and then allowed to stand until it was separated into two layers. Of the two layers, a chloroform layer in which the monomers of the methylated polymer were dissolved was collected, and the components of the polymer were analyzed by gas chromatography (GC). Benzoate was used as an internal standard. The GC conditions used at this time are shown in Table 1 below.

In order to determine the molecular weight of the polymer, GPC analysis was performed. For this purpose, polymer extraction and purification were carried out as follows. The microbial cells from which moisture was removed were collected in a cylindrical filter paper, and then extracted with a chloroform solvent at 60° C. for 4 hours or more using a Soxhlet extractor, After extraction, chloroform as a solvent was removed using an evaporator to obtain a film-type polymer. In order to purify this, the film-type polymer was dissolved 5 ml of chloroform, and then dropped little by little in 100 ml of methanol at 4° C. to remove impurities.

The molecular weight of the polymer thus purified was confirmed by GPC analysis. Specifically, the purified polymer was dissolved in chloroform at a concentration of 1 to 2 mg/mL, and then filtered through a 0.45 μm syringe filter and analyzed using GPC (Waters E0813X) equipment for chloroform. Chloroform was flowed as a mobile phase at a rate of 1 mL/min, the column temperature was adjusted to 35° C. and it was detected using RI refractive index detector. Thus, the number average molecular weight (Mn), the weight average molecular weight (Mw), the maximum peak molecular weight (Mp), and the polydispersity index (PDI) of the biopolymer composition of the present invention were measured, respectively.

| GC analysis conditions | |
| --- | --- |
| Item | Quality |
| Model | Hewlett Packard 6890N |
| Detector | Flame ionization detector(FID) |
| Column | Alltech Capillary AT ™-WAX, 30 m, 0.53 mm |
| Liquid phase | 100% polyethylene Glycol |
| Inj. port temp/Det. port temp | 250° C./250° C. |
| Carrier gas | He |
| Total flow | 3 ml/min |
| septum purge vent flow | 1 ml/min |
| Column head pressure | 29 kPa |
| Injection port mode | Splitless |
| Injection volume/Solvent | 1 μL/chloroform |
| Initial temp/Time | 80° C./5 min |
| Final temp/Time | 230° C./5 min |
| Ramp of temp. | 7.5° C./min |

The results obtained in the GC analysis are shown in Table 2 below.

TABLE 2

| IPTG induction time | LA mol content in polymer (%) | PHA content in a cell (%) | Weight Average Molecular Weight Mw($\times 10^4$) | Number Average Molecular Weight Mn($\times 10^4$) | Maximum Peak Molecular Weight Mp($\times 10^4$) | Polydispersity index PDI |
| --- | --- | --- | --- | --- | --- | --- |
| 24 hr | 13.3 ± 0.4 | P(3HP-b-LA): 29.9 ± 2.2 | 5.09 | 2.02 | 3.87 | 2.52 |
| No induction | 0.1 | P(3HP): 43.9 ± 2.9 | 9.18 | 3.87 | 8.43 | 2.38 |

As shown in Table 2, when IPTG induction was performed using the transformed recombinant strain according to the present invention, it can be confirmed that a 3-hydroxypropionate-lactic acid block copolymer was produced. However, when IPTG induction was not performed, it can be seen that only P(3HP) was produced, and LA was substantially not produced.

Experimental Example 2. Confirming a Copolymer is a Block Copolymer

In order to confirm whether the polymer prepared as described above is a P(3HP-b-LA) block copolymer, the test was performed using a differential scanning calorimeter (DSC Q100, TA instrument) together with P(3HP-r-LA) random copolymer, and the results were compared.

As a comparative example, a P(3HP-r-LA) random copolymer was prepared by the following method. First, as a vector for the comparative example, rec-GK and CPPT-540 were put in a pBluescript based vector and not an IPTG induction vector, and the prepared pBlue-reC_GK-CPPCT540 was used.

Specifically, as the PHA synthase gene for the preparation of pBlue-reC_GK-CPPCT540, PHA synthase variant derived from Cupriavidus necator (Ralstonia eutropha) (5506G. A510K) was used (reC_GK). The vector used was pBluescript II (Stratagene Co., USA).

In order to express ReC_GK, in the pSYL105 vector (Lee et al., Biotech. Bioeng., 1994, 44: 1337-1347), DNA fragments containing PHB-producing operons derived from Ralstonia eutropha H16 were digested with BamHI/EcoRI, and inserted into the BamHI/EcoRI recognition site of pBluescript II (Stratagene Co., USA). Thereby, pReCAB recombinant vector was prepared. In the pReCAB vector, PHA synthase (phaCRE) and monomer-supplying enzyme (phaARE and phaBRE) were constantly expressed by the PHB operon promoter. ReC synthase gene of pReCAB vector was completely removed by BstBI/SbfI restriction enzyme, and a variant ReC_GK synthase gene was inserted at this position. For amplification of this ReC_GK synthase gene fragment, PCR was performed using the primers [(5'-cgctaa TTCGAA tagtgacggcagagagacaatcaaatc atggcgaccggcaaaggc-3' (SEQ ID NO: 38) and 5'-caattg CCTGCAGG tcatgccttggctttgacgtatcgccc-3' (SEQ ID NO: 39)] to obtain the amplified 1.8 kb gene fragment. This was treated with restriction enzymes BstBI/SbfI, mixed with the plasmid fragment, to which T4 DNA ligase (available from. Takara) was added, allowed to react at 4° C., and inserted into a BstBI/SbfI recognition site to prepare a pBlue-reC_GK recombinant vector.

In order to construct a constantly expressed system of the operon form in which propionyl-CoA transferase were expressed together here, propionyl-CoA transferase variant (CPPCT540) derived from Clostridium propionicum was used. In order to amplify the CPPCT540 gene fragment, PCR was performed using primers [5'-caat-tgCCTGCAGGcggataacaatttcacacaggaaacagaattcat-gagaaaggttcccattatt-3' (SEQ ID NO: 40), 5'-ccatat catatg ttaggacttcatttcctt-3'(SEQ ID NO: 41)], and the obtained 1.5 kb fragment was used. This PCR fragment was treated with restriction enzymes SbfI/NdeI, then mixed with the pBlue-reC_GK recombinant plasmid fragment, to which T4 DNA ligase was added, allowed to react at 4° C. and inserted into the SbfI/NdeI recognition site to prepare a pBlue-rec_GK-CPPCT540 recombinant vector. The preparation method and cleavage map of the pBlue-rec_GK-CPPCT540 recombinant vector are shown in FIG. 6.

Polymer-producing microorganisms were made so that lactate monomer was supplied during culture using E. coli XL1-Blue wild-type strain from which ldhA has not been deleted. The carbon source used for the culture was glucose. 3HP (3-hydroxypropionate)monomer was added at 0.5 g/L to biosynthesize the P(3HP-r-LA) random copolymer. MR medium, culture time and temperature were applied to the same conditions as the block polymer synthesis described in Example 3.

The copolymer according to the present invention prepared in Example 3 and the random copolymer prepared as described above were tested using a differential scanning calorimeter (DSC Q100, TA Instrument) and the measurement was performed by raising the temperature from −40° C. to 220° C. at a temperature rise rate of 10° C./min. The results are shown in FIGS. 4 and 5.

As can be seen in FIGS. 4 and 5, for the P(3HP-b-LA) block copolymer of the present invention, both the glass transition temperature (Tg) and melting temperature (Tm) of P(3HP) and PLA are specified, whereas for the P(3HP-r-LA) random copolymer of the comparative example, Tg was found at the intermediate position between P(3HP) and PLA, and Tm was not measured. Therefore, it was clearly confirmed that the copolymer prepared according to the present invention was P(3HP-b-LA) block copolymer.

The invention claimed is:

1. A 3-hydroxypropionate-lactate block copolymer [P(3HP-b-LA)] containing lactate and 3-hydroxypropionate as repeat units, wherein the 3-hydroxypropionate-lactate block copolymer [P(3HP-b-LA)] has a lactate monomer content of 10 mol % or more.

* * * * *